US012758238B2

(12) United States Patent
Al-Jadda et al.

(10) Patent No.: US 12,758,238 B2
(45) Date of Patent: Oct. 13, 2026

(54) THROMBUS REMOVAL SYSTEMS AND ASSOCIATED METHODS

(71) Applicant: Shifamed Holdings, LLC, Campbell, CA (US)

(72) Inventors: Aadel Al-Jadda, San Carlos, CA (US); Amr Salahieh, Saratoga, CA (US); Oscar Williams, Los Gatos, CA (US); Paul Gunning, Montara, CA (US); Nicholas Lyford, Saratoga, CA (US); Tom Saul, Portland, OR (US)

(73) Assignee: Shifamed Holdings, LLC, Campbell, CA (US)

( * ) Notice: Subject to any disclaimer, the term of this patent is extended or adjusted under 35 U.S.C. 154(b) by 0 days.

(21) Appl. No.: 18/864,484

(22) PCT Filed: May 10, 2023

(86) PCT No.: PCT/US2023/066826
§ 371 (c)(1),
(2) Date: Nov. 8, 2024

(87) PCT Pub. No.: WO2023/220633
PCT Pub. Date: Nov. 16, 2023

(65) Prior Publication Data

US 2025/0302493 A1 Oct. 2, 2025

Related U.S. Application Data

(60) Provisional application No. 63/340,218, filed on May 10, 2022.

(51) Int. Cl.

| | |
|---|---|
| ***A61B 17/22*** | (2006.01) |
| ***A61B 17/00*** | (2006.01) |

(52) U.S. Cl.
CPC ........ *A61B 17/22* (2013.01); *A61B 17/00234* (2013.01); *A61B 2017/00238* (2013.01);
(Continued)

(58) Field of Classification Search
CPC .............. A61B 17/22; A61B 17/00234; A61B 2017/00238; A61B 2017/00305;
(Continued)

(56) References Cited

U.S. PATENT DOCUMENTS

| | | | |
|---|---|---|---|
| 4,006,745 | A | 2/1977 | Sorenson et al. |
| 4,148,307 | A | 4/1979 | Utsugi |

(Continued)

FOREIGN PATENT DOCUMENTS

| | | | |
|---|---|---|---|
| CN | 102727643 | A | 10/2012 |
| CN | 103417261 | A | 10/2013 |

(Continued)

OTHER PUBLICATIONS

Srivathsa et al.; U.S. Appl. No. 19/123,721 entitled "Clot visualization and workflows utilizing real-time imaging for thrombus removal systems and methods," filed Apr. 23, 2025.

(Continued)

*Primary Examiner* — Phong Son H Dang
(74) *Attorney, Agent, or Firm* — Shay Glenn LLP

(57) ABSTRACT

The present technology relates to systems and methods for removing a thrombus from a blood vessel of a patient. In some embodiments, the present technology is directed to systems including an elongated catheter having a distal portion configured to be positioned within the blood vessel of the patient, a proximal portion configured to be external to the patient, and a lumen extending therebetween. The system can also include a fluid delivery mechanism coupled
(Continued)

with a fluid lumen and configured to apply fluid, including a particularized media, to at least partially fragment the thrombus.

19 Claims, 13 Drawing Sheets

(52) U.S. Cl.
CPC ............... *A61B 2017/00305* (2013.01); *A61B 2017/22079* (2013.01); *A61B 2017/22084* (2013.01); *A61B 2217/005* (2013.01)

(58) Field of Classification Search
CPC ........... A61B 2017/22079; A61B 2017/22084; A61B 2217/005; A61M 25/0071; A61M 25/0074; A61M 25/0026; A61M 1/77
See application file for complete search history.

(56) References Cited

U.S. PATENT DOCUMENTS 4,577,621 A 3/1986 Patel
4,954,251 A 9/1990 Barnes et al.
5,114,581 A 5/1992 Goldsmith et al.
5,135,482 A 8/1992 Neracher
5,651,776 A 7/1997 Appling et al.
5,662,671 A 9/1997 Barbut et al.
5,788,647 A 8/1998 Eggers
5,795,322 A 8/1998 Boudewijn et al.
5,989,271 A 11/1999 Bonnette et al.
5,993,469 A 11/1999 McKenzie et al.
6,004,339 A 12/1999 Wijay
6,053,870 A 4/2000 Fulton, III
6,059,825 A 5/2000 Hobbs et al.
6,074,374 A 6/2000 Fulton
6,086,534 A 7/2000 Kesten
6,228,052 B1 5/2001 Pohndorf
6,283,950 B1 9/2001 Appling
6,287,333 B1 9/2001 Appling et al.
6,306,163 B1 10/2001 Fitz
6,315,762 B1 11/2001 Recinella et al.
6,361,545 B1 3/2002 Macoviak et al.
6,524,300 B2 2/2003 Meglin
RE38,074 E 4/2003 Recinella et al.
6,582,447 B1 6/2003 Patel et al.
6,620,148 B1 * 9/2003 Tsugita ............ A61B 17/12109 604/509
6,719,717 B1 4/2004 Johnson et al.
6,733,489 B2 5/2004 Nutting et al.
6,827,701 B2 12/2004 MacMahon et al.
6,875,193 B1 4/2005 Bonnette et al.
6,881,218 B2 4/2005 Beyer et al.
6,942,635 B2 9/2005 Rosenblatt et al.
6,966,886 B2 11/2005 Appling
7,033,347 B2 4/2006 Appling
7,131,981 B2 11/2006 Appling et al.
7,163,533 B2 1/2007 Hobbs et al.
7,217,256 B2 5/2007 Di Palma
7,220,269 B1 5/2007 Ansel et al.
7,273,478 B2 9/2007 Appling et al.
7,279,000 B2 10/2007 Cartier et al.
7,344,533 B2 3/2008 Pearson et al.
7,347,852 B2 3/2008 Hobbs et al.
7,419,487 B2 9/2008 Johnson et al.
7,422,586 B2 9/2008 Morris et al.
7,455,675 B2 11/2008 Schur et al.
7,458,967 B2 12/2008 Appling et al.
7,483,457 B2 1/2009 Howe et al.
7,544,202 B2 6/2009 Cartier et al.
D595,892 S 7/2009 Smith et al.
7,563,247 B2 7/2009 Maguire et al.
D603,044 S 10/2009 Appling et al.
7,618,411 B2 11/2009 Appling
7,717,900 B2 5/2010 di Palma
7,722,635 B2 5/2010 Beyer et al.
7,740,616 B2 6/2010 Smith et al.
7,765,010 B2 7/2010 Chornenky et al.
7,766,961 B2 8/2010 Patel et al.
7,771,401 B2 8/2010 Hekmat et al.
7,780,628 B1 8/2010 Keren et al.
D626,231 S 10/2010 Perchik
7,826,904 B2 11/2010 Appling et al.
7,833,215 B2 11/2010 Appling
RE42,016 E 12/2010 Chornenky et al.
D630,321 S 1/2011 Hamilton
D631,154 S 1/2011 Hamilton
7,914,503 B2 3/2011 Goodson et al.
RE42,277 E 4/2011 Jaafar et al.
7,938,824 B2 5/2011 Chornenky et al.
7,942,873 B2 5/2011 Kwan et al.
7,947,019 B2 5/2011 Perchik et al.
D640,788 S 6/2011 Appling
7,993,325 B2 8/2011 Elkins et al.
D644,735 S 9/2011 Elbe et al.
RE42,835 E 10/2011 Chornenky et al.
RE43,009 E 12/2011 Chornenky et al.
D650,475 S 12/2011 Smith et al.
8,114,070 B2 2/2012 Rubinsky et al.
8,167,903 B2 5/2012 Hardert et al.
8,231,603 B2 7/2012 Hobbs et al.
8,241,343 B2 8/2012 Douglass et al.
8,317,773 B2 11/2012 Appling et al.
8,328,760 B2 12/2012 Lareau
8,328,768 B2 12/2012 Quigley et al.
8,337,451 B2 12/2012 Lareau et al.
8,337,470 B2 12/2012 Prasad et al.
8,366,687 B2 2/2013 Girard et al.
8,372,064 B2 2/2013 Douglass et al.
8,377,011 B2 2/2013 Weaver et al.
D677,798 S 3/2013 Hart et al.
8,425,455 B2 4/2013 Nentwick
8,472,011 B2 6/2013 Cronin et al.
8,475,488 B2 7/2013 Cartier et al.
8,496,644 B2 7/2013 Graffam et al.
8,506,512 B2 8/2013 Aklog et al.
8,518,011 B2 8/2013 Goodson et al.
8,535,306 B2 9/2013 Pearson et al.
8,574,204 B2 11/2013 Bourne et al.
8,585,678 B2 11/2013 Elkins et al.
8,585,950 B2 11/2013 Appling et al.
8,586,897 B2 11/2013 Cronin
8,603,070 B1 12/2013 Lareau et al.
8,607,428 B2 12/2013 Nentwick et al.
8,613,717 B2 12/2013 Aklog et al.
8,632,534 B2 1/2014 Pearson et al.
8,663,116 B2 3/2014 Hamilton
8,679,074 B2 3/2014 Daly et al.
8,734,374 B2 5/2014 Aklog et al.
8,734,439 B2 5/2014 Gough et al.
8,753,292 B2 6/2014 Ingold et al.
8,753,335 B2 6/2014 Moshe et al.
8,784,402 B1 7/2014 Lareau et al.
8,858,497 B2 10/2014 Di Palma et al.
8,864,754 B2 10/2014 Appling et al.
8,903,488 B2 12/2014 Callas et al.
8,926,573 B2 1/2015 Smith et al.
8,956,383 B2 2/2015 Aklog et al.
8,992,513 B2 3/2015 Delaney
9,033,914 B2 5/2015 Haarala et al.
9,050,435 B2 6/2015 Lareau et al.
9,055,964 B2 6/2015 Cartier et al.
9,078,665 B2 7/2015 Moss et al.
9,084,619 B2 7/2015 Cronin et al.
D736,916 S 8/2015 Appling et al.
9,149,607 B2 10/2015 Scheibe et al.
9,161,811 B2 10/2015 Cronin
9,173,704 B2 11/2015 Hobbs et al.
9,186,491 B2 11/2015 Casiello et al.
D744,639 S 12/2015 Aklog et al.
9,205,242 B2 12/2015 Nardone et al.
9,206,283 B1 12/2015 Santerre et al.
D748,774 S 2/2016 Caron
9,254,173 B2 2/2016 Cronin et al.

(56) References Cited

U.S. PATENT DOCUMENTS

| | | | |
|---|---|---|---|
| 9,339,328 | B2 | 5/2016 | Ortiz et al. |
| 9,351,861 | B2 | 5/2016 | Sherburne |
| 9,358,378 | B2 | 6/2016 | Hanson et al. |
| 9,402,938 | B2 | 8/2016 | Aklog et al. |
| 9,408,620 | B2 | 8/2016 | Rosenbluth et al. |
| 9,414,881 | B2 | 8/2016 | Callas et al. |
| 9,440,046 | B2 | 9/2016 | Hobbs et al. |
| 9,440,047 | B1 | 9/2016 | Elberse et al. |
| 9,445,746 | B1 | 9/2016 | Elberse et al. |
| 9,447,892 | B2 | 9/2016 | Lareau et al. |
| 9,480,497 | B2 | 11/2016 | Ingold et al. |
| 9,675,406 | B2 | 6/2017 | Moss et al. |
| 9,681,909 | B2 | 6/2017 | Bhargav et al. |
| 9,700,332 | B2 | 7/2017 | Marchand et al. |
| 9,700,368 | B2 | 7/2017 | Callas et al. |
| 9,707,339 | B2 | 7/2017 | Chartrand et al. |
| 9,757,197 | B2 | 9/2017 | Cronin et al. |
| 9,764,115 | B2 | 9/2017 | Tegg |
| 9,788,896 | B2 | 10/2017 | Cronin et al. |
| 9,789,229 | B1 | 10/2017 | Lareau et al. |
| D802,409 | S | 11/2017 | Caron |
| 9,820,761 | B2 | 11/2017 | Garrison et al. |
| 9,867,908 | B2 | 1/2018 | Lareau et al. |
| 9,888,956 | B2 | 2/2018 | Model et al. |
| 9,895,189 | B2 | 2/2018 | Pearson |
| 9,895,524 | B2 | 2/2018 | Lareau |
| 9,907,613 | B2 | 3/2018 | Cronin et al. |
| 9,933,079 | B2 | 4/2018 | Weaver et al. |
| 9,999,493 | B2 | 6/2018 | Nguyen et al. |
| 10,004,531 | B2 | 6/2018 | Rosenbluth et al. |
| 10,010,666 | B2 | 7/2018 | Rubinsky et al. |
| 10,039,900 | B2 | 8/2018 | di Palma et al. |
| 10,045,790 | B2 | 8/2018 | Cox et al. |
| 10,098,651 | B2 | 10/2018 | Marchand et al. |
| 10,105,477 | B2 | 10/2018 | Davey et al. |
| 10,159,830 | B2 | 12/2018 | Miller |
| 10,166,321 | B2 | 1/2019 | Casiello et al. |
| 10,188,831 | B2 | 1/2019 | Elberse et al. |
| 10,238,406 | B2 | 3/2019 | Cox et al. |
| D847,623 | S | 5/2019 | Caron |
| 10,279,112 | B2 | 5/2019 | Houde et al. |
| 10,349,960 | B2 | 7/2019 | Quick |
| D860,941 | S | 9/2019 | Wheeler |
| 10,429,517 | B1 | 10/2019 | Isham et al. |
| 10,492,805 | B2 | 12/2019 | Culbert et al. |
| 10,493,257 | B2 | 12/2019 | Chartrand et al. |
| 10,500,329 | B2 | 12/2019 | Weaver et al. |
| 10,517,617 | B2 | 12/2019 | Aklog et al. |
| 10,517,633 | B2 | 12/2019 | Nash et al. |
| D879,957 | S | 3/2020 | Zabar et al. |
| 10,610,678 | B2 | 4/2020 | Martin |
| 10,660,691 | B2 | 5/2020 | McKernon et al. |
| 10,782,425 | B2 | 9/2020 | Isham |
| 10,786,270 | B2 | 9/2020 | Yang et al. |
| 10,792,056 | B2 | 10/2020 | Vale et al. |
| 10,806,896 | B2 | 10/2020 | Davies et al. |
| 10,835,715 | B2 | 11/2020 | Cruz et al. |
| D908,204 | S | 1/2021 | Casiello et al. |
| 10,905,492 | B2 | 2/2021 | Neal |
| 10,912,885 | B2 | 2/2021 | Maguire et al. |
| D916,280 | S | 4/2021 | Swift |
| D916,281 | S | 4/2021 | Swift |
| 11,000,682 | B2 | 5/2021 | Merritt et al. |
| 11,065,018 | B2 | 7/2021 | Buck et al. |
| 11,154,314 | B2 | 10/2021 | Quick |
| 11,241,564 | B2 | 2/2022 | Casiello et al. |
| 11,259,824 | B2 | 3/2022 | Brady et al. |
| 11,348,250 | B2 | 5/2022 | Koster et al. |
| 11,433,218 | B2 | 9/2022 | Quick et al. |
| 11,497,889 | B2 | 11/2022 | Mixter et al. |
| D972,720 | S | 12/2022 | Cote et al. |
| D972,723 | S | 12/2022 | Swift et al. |
| 11,559,382 | B2 | 1/2023 | Merritt et al. |
| 11,607,150 | B2 | 3/2023 | Schweikert et al. |
| 11,648,020 | B2 | 5/2023 | Cote et al. |
| 11,710,242 | B2 | 7/2023 | Wang et al. |
| 11,730,924 | B2 | 8/2023 | Saadat et al. |
| 11,832,837 | B2 | 12/2023 | Hauser |
| 11,864,779 | B2 | 1/2024 | Dinh |
| 11,890,046 | B2 | 2/2024 | Neal et al. |
| 11,950,835 | B2 | 4/2024 | O'Brien et al. |
| 11,954,887 | B2 | 4/2024 | Blau |
| 11,957,405 | B2 | 4/2024 | Pearson |
| 11,986,196 | B2 | 5/2024 | Wallace et al. |
| 11,992,643 | B2 | 5/2024 | Lee et al. |
| 11,998,223 | B2 | 6/2024 | Brady et al. |
| 12,001,605 | B2 | 6/2024 | Yee et al. |
| 12,002,065 | B2 | 6/2024 | Look et al. |
| 12,004,731 | B2 | 6/2024 | Duffy et al. |
| 12,011,186 | B2 | 6/2024 | Stefanov |
| 12,016,580 | B2 | 6/2024 | Quick et al. |
| 12,023,058 | B2 | 7/2024 | Casey |
| 12,029,442 | B2 | 7/2024 | O'Malley |
| 12,032,735 | B2 | 7/2024 | Rubin et al. |
| 12,042,160 | B2 | 7/2024 | Yang et al. |
| 12,048,446 | B2 | 7/2024 | Dwivedi et al. |
| 12,053,192 | B2 | 8/2024 | Baron et al. |
| 12,053,685 | B2 | 8/2024 | Lockhart et al. |
| 12,064,130 | B2 | 8/2024 | O'Malley et al. |
| 12,076,037 | B2 | 9/2024 | Brady et al. |
| 12,080,020 | B2 | 9/2024 | Blau |
| 12,096,938 | B2 | 9/2024 | Hettel et al. |
| 12,096,951 | B2 | 9/2024 | Barry et al. |
| 12,097,345 | B2 | 9/2024 | Schultz et al. |
| 12,133,657 | B2 | 11/2024 | Vale et al. |
| 12,144,515 | B2 | 11/2024 | Nagireiter et al. |
| 12,150,659 | B2 | 11/2024 | Look et al. |
| 12,156,665 | B2 | 12/2024 | Look et al. |
| 12,156,666 | B2 | 12/2024 | Trosper et al. |
| 12,156,667 | B2 | 12/2024 | Trosper et al. |
| 12,171,449 | B2 | 12/2024 | Lee |
| 12,184,353 | B2 | 12/2024 | Collins |
| 12,186,064 | B2 | 1/2025 | Strasser et al. |
| 12,198,330 | B2 | 1/2025 | Blau |
| 12,201,506 | B2 | 1/2025 | Buck et al. |
| 12,213,691 | B2 | 2/2025 | Whelan |
| 12,214,189 | B2 | 2/2025 | Lorenzo et al. |
| 12,220,138 | B2 | 2/2025 | Whelan |
| 12,246,141 | B2 | 3/2025 | Saadat et al. |
| 12,251,119 | B2 | 3/2025 | Naglreiter et al. |
| D1,069,809 | S | 4/2025 | Strasser et al. |
| 12,274,834 | B2 | 4/2025 | Saadat et al. |
| 12,305,990 | B2 | 5/2025 | Collins |
| D1,077,996 | S | 6/2025 | Yang et al. |
| 12,329,397 | B2 | 6/2025 | Bartholomew et al. |
| 12,343,479 | B2 | 7/2025 | Yang et al. |
| 12,343,486 | B2 | 7/2025 | Casey et al. |
| 12,349,935 | B1 | 7/2025 | Pons |
| 12,350,443 | B2 | 7/2025 | Yee et al. |
| 12,364,503 | B2 | 7/2025 | Pons |
| 12,369,940 | B2 | 7/2025 | Jenson et al. |
| 12,376,904 | B1 | 8/2025 | Stern et al. |
| 12,376,928 | B2 | 8/2025 | Lau et al. |
| 12,402,902 | B2 | 9/2025 | Vale et al. |
| 12,414,784 | B1 | 9/2025 | Li et al. |
| 12,419,657 | B2 | 9/2025 | Yang et al. |
| 12,419,703 | B2 | 9/2025 | O'Malley et al. |
| 12,440,230 | B2 | 10/2025 | Gamba et al. |
| 12,440,289 | B2 | 10/2025 | Lau et al. |
| 12,446,908 | B2 | 10/2025 | Dwivedi et al. |
| 12,446,979 | B2 | 10/2025 | Yang et al. |
| 12,447,317 | B2 | 10/2025 | Lau et al. |
| 12,447,319 | B2 | 10/2025 | Connolly |
| 12,453,564 | B2 | 10/2025 | Buck et al. |
| 12,458,380 | B2 | 11/2025 | Dwivedi et al. |
| 12,462,425 | B2 | 11/2025 | Blau |
| 12,465,383 | B2 | 11/2025 | Casey et al. |
| 12,465,393 | B1 | 11/2025 | Pons |
| 12,468,215 | B2 | 11/2025 | Rosenthal et al. |
| 12,471,941 | B2 | 11/2025 | Brady et al. |
| 12,478,390 | B2 | 11/2025 | Janardhan et al. |
| 12,502,185 | B2 | 12/2025 | Teigen et al. |
| 12,521,132 | B2 | 1/2026 | Teigen et al. |
| 12,521,134 | B2 | 1/2026 | Gilvarry et al. |

(56) References Cited

U.S. PATENT DOCUMENTS 12,521,479 B2 1/2026 Casey et al.
12,527,586 B2 1/2026 Keating et al.
12,527,587 B2 1/2026 Saadat et al.
12,539,127 B2 2/2026 Look et al.
12,539,130 B2 2/2026 Casey et al.
12,558,175 B2 2/2026 Lau et al.
12,564,414 B2 3/2026 Yang et al.
12,564,458 B2 3/2026 Yang et al.
12,636,022 B2 5/2026 Bartholomew et al.
12,642,950 B2 6/2026 Verma et al.
12,653,555 B2 6/2026 Look et al.
12,653,990 B2 6/2026 Conlon
12,667,695 B2 6/2026 Saadat et al.
12,678,249 B2 7/2026 Bartholomew et al.
2002/0058904 A1 5/2002 Boock et al.
2002/0111579 A1 8/2002 Moutafis et al.
2002/0123761 A1 9/2002 Barbut et al.
2002/0132076 A1 9/2002 Stevens
2003/0065250 A1 4/2003 Chiel et al.
2003/0104073 A1* 6/2003 Johansson .............. A61K 33/00 604/509
2003/0199865 A1* 10/2003 Knudson .......... A61B 17/12186 606/41
2003/0236517 A1 12/2003 Appling
2004/0097880 A1 5/2004 Schur
2005/0027262 A1 2/2005 Appling et al.
2005/0131343 A1 6/2005 Abrams et al.
2005/0143687 A1 6/2005 Rosenblatt et al.
2005/0165364 A1 7/2005 DiMatteo et al.
2005/0171510 A1 8/2005 DiCarlo et al.
2005/0245894 A1* 11/2005 Zadno-Azizi ...... A61M 25/1011 604/509
2006/0041304 A1 2/2006 Jang et al.
2006/0184141 A1 8/2006 Smith et al.
2006/0270974 A1 11/2006 Goff et al.
2006/0282119 A1 12/2006 Perchik
2006/0293725 A1 12/2006 Rubinsky et al.
2006/0293730 A1 12/2006 Rubinsky et al.
2006/0293731 A1 12/2006 Rubinsky et al.
2007/0021685 A1 1/2007 Oepen et al.
2007/0037132 A1 2/2007 Sukavaneshvar et al.
2007/0078391 A1 4/2007 Wortley et al.
2007/0106162 A1 5/2007 Illyes et al.
2007/0156135 A1 7/2007 Rubinsky et al.
2007/0173786 A1 7/2007 Recinella et al.
2007/0191825 A1 8/2007 Cronin et al.
2007/0198035 A1 8/2007 Threlkeld
2007/0282303 A1 12/2007 Nash et al.
2008/0114308 A1 5/2008 di Palma et al.
2008/0132884 A1 6/2008 Rubinsky et al.
2008/0132885 A1 6/2008 Rubinsky et al.
2008/0154186 A1 6/2008 Appling et al.
2008/0167649 A1 7/2008 Edwards et al.
2008/0167678 A1 7/2008 Morsi
2008/0172080 A1 7/2008 Isham
2008/0183202 A1 7/2008 Isham
2008/0208180 A1 8/2008 Cartier et al.
2008/0208236 A1 8/2008 Hobbs et al.
2008/0269774 A1 10/2008 Garcia et al.
2008/0287939 A1 11/2008 Appling et al.
2008/0294188 A1 11/2008 Appling et al.
2008/0300619 A1 12/2008 Isham
2008/0306499 A1 12/2008 Katoh et al.
2009/0005747 A1 1/2009 Michaels et al.
2009/0024190 A1 1/2009 Irvine
2009/0038752 A1 2/2009 Weng et al.
2009/0048577 A1 2/2009 Gillies et al.
2009/0076585 A1 3/2009 Hendriksen et al.
2009/0118683 A1 5/2009 Hanson et al.
2009/0131924 A1 5/2009 Meyer et al.
2009/0163926 A1 6/2009 Sos
2009/0171267 A1 7/2009 Bonnette et al.
2009/0221899 A1 9/2009 Isham
2009/0259220 A1 10/2009 Appling et al.
2009/0281477 A1 11/2009 Mikus et al.
2009/0306606 A1 12/2009 Lancette et al.
2009/0306625 A1 12/2009 Pereira-Kamath et al.
2009/0314724 A1 12/2009 Nierich
2010/0004623 A1 1/2010 Hamilton et al.
2010/0022947 A1 1/2010 Hassidov et al.
2010/0076302 A1 3/2010 Gray et al.
2010/0094201 A1 4/2010 Mallaby
2010/0114063 A1 5/2010 Recinella et al.
2010/0152725 A1 6/2010 Pearson et al.
2010/0168642 A1 7/2010 Appling et al.
2010/0204712 A1 8/2010 Mallaby
2010/0249505 A1 9/2010 Shoham et al.
2010/0249771 A1 9/2010 Pearson et al.
2010/0249815 A1 9/2010 Jantzen et al.
2010/0250209 A1 9/2010 Pearson et al.
2010/0256487 A1 10/2010 Hawkins et al.
2010/0256546 A1 10/2010 Davis et al.
2010/0256630 A1 10/2010 Hamilton et al.
2011/0004295 A1 1/2011 Wittens
2011/0034886 A1 2/2011 Elbe et al.
2011/0040321 A1 2/2011 Cartier
2011/0060316 A1 3/2011 DiCarlo
2011/0105823 A1 5/2011 Single et al.
2011/0112527 A1 5/2011 Hamilton et al.
2011/0172644 A1 7/2011 Zanoni et al.
2011/0190734 A1 8/2011 Graffam et al.
2011/0190806 A1 8/2011 Wittens
2011/0213392 A1 9/2011 Aklog et al.
2011/0238057 A1 9/2011 Moss et al.
2011/0288529 A1 11/2011 Fulton
2012/0059210 A1 3/2012 Frassica
2012/0078232 A1 3/2012 Schulting
2012/0101471 A1 4/2012 di Palma et al.
2012/0172655 A1 7/2012 Campbell et al.
2012/0178986 A1 7/2012 Campbell et al.
2012/0184942 A1 7/2012 Lareau
2012/0193255 A1 8/2012 Lareau et al.
2012/0226271 A1 9/2012 Callas et al.
2012/0310230 A1 12/2012 Willis
2013/0131691 A1 5/2013 Kozak et al.
2013/0150811 A1 6/2013 Horgan
2013/0190602 A1 7/2013 Liao et al.
2013/0304082 A1 11/2013 Aklog et al.
2013/0310845 A1 11/2013 Thor et al.
2013/0324943 A1 12/2013 Weaver et al.
2013/0338608 A1 12/2013 Moorehead et al.
2014/0005699 A1 1/2014 Bonnette et al.
2014/0042154 A1 2/2014 Cronin
2014/0074049 A1 3/2014 Veldhuijzen et al.
2014/0142617 A1 5/2014 Larsen
2014/0228869 A1 8/2014 Bonnette et al.
2014/0303658 A1 10/2014 Bonnette et al.
2014/0358060 A1 12/2014 Laster
2014/0364896 A1 12/2014 Consigny
2014/0377738 A1 12/2014 Bachmann et al.
2015/0057648 A1 2/2015 Swift et al.
2015/0068941 A1 3/2015 Caron
2015/0150589 A1 6/2015 Yamanouchi
2015/0190615 A1 7/2015 Shaltis
2015/0230810 A1 8/2015 Creighton et al.
2015/0272622 A1 10/2015 Carson et al.
2015/0305810 A1 10/2015 McElwee et al.
2015/0313732 A1* 11/2015 Fulton, III ................ A61F 2/82 623/1.11
2015/0320488 A1 11/2015 Moshe et al.
2015/0359547 A1 12/2015 Vale et al.
2016/0022371 A1 1/2016 Sauer et al.
2016/0030708 A1 2/2016 Casiello et al.
2016/0038174 A1 2/2016 Bruzzi et al.
2016/0058493 A1 3/2016 Neal et al.
2016/0106501 A1 4/2016 Appling
2016/0114128 A1 4/2016 Lancette
2016/0114129 A1 4/2016 Lancette
2016/0135712 A1 5/2016 Holochwost et al.
2016/0135829 A1 5/2016 Holochwost et al.
2016/0235974 A1 8/2016 Holochwost et al.
2016/0262777 A1* 9/2016 Stigall ...................... A61N 7/00
2016/0271321 A1 9/2016 Chambers et al.
2016/0279393 A1 9/2016 Anderson et al.

(56) References Cited

U.S. PATENT DOCUMENTS

2016/0296747 A1 10/2016 Glenn et al.
2016/0317797 A1 11/2016 Smith et al.
2016/0346472 A1 12/2016 Mitchell et al.
2017/0035445 A1 2/2017 Nguyen et al.
2017/0039711 A1 2/2017 Dincer et al.
2017/0136158 A1 5/2017 Culhane et al.
2017/0172603 A1 6/2017 Bonnette et al.
2017/0215890 A1 8/2017 Trujman et al.
2017/0231655 A1 8/2017 Aljuri et al.
2017/0303939 A1 10/2017 Greenhalgh et al.
2017/0303949 A1 10/2017 Ribo Jacobi et al.
2017/0333060 A1 11/2017 Panian
2017/0333076 A1 11/2017 Bruzzi et al.
2018/0064526 A1 3/2018 Walzman
2018/0071014 A1 3/2018 Neal et al.
2018/0071492 A1 3/2018 Laby et al.
2018/0098782 A1 4/2018 Farago
2018/0103974 A1 4/2018 Osborne et al.
2018/0116710 A1 5/2018 Pearson
2018/0207397 A1* 7/2018 Look ................. A61M 25/0032
2018/0272050 A1 9/2018 Laureau et al.
2018/0291882 A1 10/2018 Algawi et al.
2018/0317899 A1 11/2018 Zada
2018/0344987 A1 12/2018 Lancette et al.
2019/0008550 A1 1/2019 Yamanouchi
2019/0021856 A1 1/2019 High
2019/0029791 A1 1/2019 Walzman
2019/0030319 A1 1/2019 Raines
2019/0038300 A1 2/2019 Savastano et al.
2019/0054284 A1 2/2019 Smith et al.
2019/0059840 A1 2/2019 Fouras et al.
2019/0076623 A1 3/2019 Mackay et al.
2019/0083169 A1 3/2019 Single et al.
2019/0143085 A1 5/2019 Sham
2019/0167287 A1 6/2019 Vale et al.
2019/0175939 A1 6/2019 Isham et al.
2019/0217058 A1 7/2019 Swift
2019/0262031 A1 8/2019 Efremkin
2019/0290323 A1 9/2019 Chun et al.
2019/0321656 A1 10/2019 Isham et al.
2019/0365248 A1 12/2019 Mueller et al.
2019/0365395 A1 12/2019 Tran et al.
2019/0365464 A1 12/2019 Govari et al.
2020/0022712 A1 1/2020 Deville et al.
2020/0030501 A1 1/2020 Minskoff
2020/0038042 A1 2/2020 Al-Shraideh
2020/0038057 A1 2/2020 Rai et al.
2020/0054864 A1 2/2020 Vrancken Peeters et al.
2020/0085453 A1 3/2020 Porter et al.
2020/0101326 A1 4/2020 Zeringue
2020/0107843 A1 4/2020 Goertz et al.
2020/0164117 A1 5/2020 Culhane et al.
2020/0237981 A1 7/2020 Tuval et al.
2020/0246014 A1 8/2020 Walzman
2020/0253670 A1 8/2020 Doisneau et al.
2020/0261266 A1* 8/2020 Bley .................... A61K 9/1652
2020/0276415 A1 9/2020 Tang et al.
2020/0281611 A1 9/2020 Kelly et al.
2020/0289722 A1 9/2020 Culbert et al.
2020/0320775 A1 10/2020 Holladay et al.
2020/0352286 A1 11/2020 Galindo et al.
2020/0367917 A1 11/2020 Teigen et al.
2020/0397959 A1 12/2020 Douglas et al.
2021/0001090 A1 1/2021 Tran et al.
2021/0008354 A1 1/2021 Bhamanyar
2021/0022843 A1* 1/2021 Hauser ................. A61B 17/221
2021/0068854 A1 3/2021 Wallace
2021/0069468 A1 3/2021 Keating et al.
2021/0085931 A1 3/2021 Green et al.
2021/0106346 A1 4/2021 Wallace et al.
2021/0121188 A1 4/2021 Yurek
2021/0128182 A1 5/2021 Teigen et al.
2021/0128893 A1 5/2021 Twomey et al.
2021/0138194 A1 5/2021 Garrison et al.
2021/0145445 A9 5/2021 Goldsmith
2021/0153884 A1 5/2021 Casey et al.
2021/0154433 A1 5/2021 Casey et al.
2021/0186537 A1 6/2021 Buck et al.
2021/0186541 A1 6/2021 Thress
2021/0186547 A1 6/2021 Kassab et al.
2021/0196292 A1 7/2021 Vale
2021/0220006 A1 7/2021 Mitchell
2021/0236257 A1 8/2021 Walzman
2021/0244698 A1 8/2021 Kalergis et al.
2021/0252274 A1 8/2021 Dhaliwal et al.
2021/0298773 A1 9/2021 Echarri et al.
2021/0315639 A1 10/2021 Manucherhabadi et al.
2021/0346040 A1 11/2021 Panian
2021/0361314 A1 11/2021 Teigen et al.
2021/0378694 A1 12/2021 Thress et al.
2021/0393277 A1 12/2021 Vale et al.
2022/0000500 A1 1/2022 Arad Hadar et al.
2022/0008022 A1 1/2022 Raman et al.
2022/0039815 A1 2/2022 Thress et al.
2022/0054151 A1 2/2022 Shifflette
2022/0061870 A1 3/2022 Mintz
2022/0061872 A1 3/2022 Mintz
2022/0105333 A1 4/2022 Bourne et al.
2022/0110634 A1 4/2022 Watanabe
2022/0125450 A1 4/2022 Sirhan et al.
2022/0142638 A1 5/2022 Enright et al.
2022/0151647 A1 5/2022 Dolendo et al.
2022/0152355 A1 5/2022 Dolendo et al.
2022/0168000 A1 6/2022 Nagireiter et al.
2022/0175404 A1 6/2022 Mintz et al.
2022/0183646 A1 6/2022 Fouras et al.
2022/0193373 A1 6/2022 Clark et al.
2022/0202506 A1 6/2022 Sganga et al.
2022/0218206 A1 7/2022 Petroff et al.
2022/0249151 A1 8/2022 Forrest et al.
2022/0257268 A1 8/2022 Culbert et al.
2022/0287729 A1 9/2022 Phillips et al.
2023/0030606 A1 2/2023 Swift et al.
2023/0088977 A1 3/2023 Fischell et al.
2023/0148876 A1 5/2023 Robinson et al.
2023/0149035 A1 5/2023 Sirhan et al.
2023/0149073 A1 5/2023 Forrest et al.
2023/0218310 A1 7/2023 Scheinblum et al.
2023/0241302 A1 8/2023 Merritt et al.
2023/0248380 A1 8/2023 Long et al.
2023/0285081 A1 9/2023 Wagner et al.
2023/0301673 A1 9/2023 Park et al.
2023/0310751 A1 10/2023 Merritt et al.
2023/0329777 A1 10/2023 Single et al.
2023/0346416 A1 11/2023 Berrada et al.
2023/0355938 A1 11/2023 Merritt et al.
2023/0364319 A1 11/2023 Vale et al.
2023/0389932 A1 12/2023 Ozenne et al.
2024/0000469 A1 1/2024 Teigen et al.
2024/0024029 A1 1/2024 Kopel et al.
2024/0074804 A1 3/2024 Neal et al.
2024/0081857 A1 3/2024 Luong et al.
2024/0082540 A1 3/2024 Brodt et al.
2024/0138903 A1 5/2024 Pearson
2024/0148956 A1 5/2024 Swift et al.
2024/0156473 A1 5/2024 Aklog et al.
2024/0157041 A1 5/2024 Zikry et al.
2024/0164800 A1 5/2024 Thio et al.
2024/0164804 A1 5/2024 Jenson et al.
2024/0164805 A1 5/2024 Jenson et al.
2024/0173042 A1 5/2024 Yang et al.
2024/0173063 A1 5/2024 Neal, II et al.
2024/0180571 A1 6/2024 Dwivedi et al.
2024/0180572 A1 6/2024 Dwivedi et al.
2024/0180635 A1 6/2024 Lau et al.
2024/0180640 A1 6/2024 Hutter et al.
2024/0180641 A1 6/2024 Lau et al.
2024/0180642 A1 6/2024 Hutter et al.
2024/0180643 A1 6/2024 Hutter et al.
2024/0180650 A1 6/2024 Lau et al.
2024/0180651 A1 6/2024 Lau et al.
2024/0180652 A1 6/2024 Lau et al.
2024/0180653 A1 6/2024 Lau et al.
2024/0180654 A1 6/2024 Lau et al.

(56) References Cited

U.S. PATENT DOCUMENTS

| | | | |
|---|---|---|---|
| 2024/0180658 | A1 | 6/2024 | Lau et al. |
| 2024/0180659 | A1 | 6/2024 | Lau et al. |
| 2024/0181207 | A1 | 6/2024 | Bartholomew et al. |
| 2024/0181208 | A1 | 6/2024 | Bartholomew et al. |
| 2024/0181209 | A1 | 6/2024 | Bartholomew et al. |
| 2024/0181213 | A1 | 6/2024 | Hutter et al. |
| 2024/0181214 | A1 | 6/2024 | Hutter et al. |
| 2024/0181224 | A1 | 6/2024 | Bartholomew et al. |
| 2024/0183382 | A1 | 6/2024 | Bartholomew et al. |
| 2024/0188972 | A1 | 6/2024 | Vale et al. |
| 2024/0188976 | A1 | 6/2024 | Gamba et al. |
| 2024/0189544 | A1 | 6/2024 | Casey et al. |
| 2024/0197347 | A1 | 6/2024 | Saadat et al. |
| 2024/0197349 | A1 | 6/2024 | Kelly et al. |
| 2024/0197416 | A1 | 6/2024 | Gonzalez et al. |
| 2024/0197418 | A1 | 6/2024 | Jourdan et al. |
| 2024/0197978 | A1 | 6/2024 | Yee |
| 2024/0198051 | A1 | 6/2024 | Jourdan et al. |
| 2024/0198060 | A1 | 6/2024 | Casey et al. |
| 2024/0198072 | A1 | 6/2024 | Merritt et al. |
| 2024/0206892 | A1 | 6/2024 | Al-Jadda et al. |
| 2024/0207570 | A1 | 6/2024 | Mar et al. |
| 2024/0216600 | A1 | 7/2024 | Lenihan et al. |
| 2024/0225674 | A1 | 7/2024 | Dederich et al. |
| 2024/0237997 | A1 | 7/2024 | Salahieh et al. |
| 2024/0238002 | A1 | 7/2024 | Al-Jadda et al. |
| 2024/0245414 | A1 | 7/2024 | Calderon et al. |
| 2024/0245417 | A1 | 7/2024 | Baron et al. |
| 2024/0245424 | A1 | 7/2024 | Casey et al. |
| 2024/0261492 | A1 | 8/2024 | Yang et al. |
| 2024/0268844 | A1 | 8/2024 | Casey et al. |
| 2024/0277308 | A1 | 8/2024 | Min et al. |
| 2024/0277354 | A1 | 8/2024 | Keating et al. |
| 2024/0277355 | A1 | 8/2024 | Vale et al. |
| 2024/0277356 | A1 | 8/2024 | Vale et al. |
| 2024/0277357 | A1 | 8/2024 | Carney et al. |
| 2024/0277358 | A1 | 8/2024 | Casey et al. |
| 2024/0277363 | A1 | 8/2024 | Keating et al. |
| 2024/0277364 | A1 | 8/2024 | Casey |
| 2024/0277914 | A1 | 8/2024 | Vale et al. |
| 2024/0285846 | A1 | 8/2024 | Su et al. |
| 2024/0285902 | A1 | 8/2024 | Pedroso et al. |
| 2024/0299048 | A1 | 9/2024 | Saadat et al. |
| 2024/0299707 | A1 | 9/2024 | Humbert et al. |
| 2024/0307659 | A1 | 9/2024 | Saadat et al. |
| 2024/0341768 | A1 | 10/2024 | Dwivedi et al. |
| 2024/0341785 | A1 | 10/2024 | Trosper et al. |
| 2024/0341786 | A1 | 10/2024 | Trosper et al. |
| 2024/0382223 | A1 | 11/2024 | Gilvarry et al. |
| 2025/0009432 | A1 | 1/2025 | Roh et al. |
| 2025/0064322 | A1 | 2/2025 | Vale et al. |
| 2025/0099116 | A1 | 3/2025 | Saadat et al. |
| 2025/0107813 | A1 | 4/2025 | Childs et al. |
| 2025/0152189 | A1 | 5/2025 | Janardhan et al. |
| 2025/0160859 | A1 | 5/2025 | Janardhan et al. |
| 2025/0169834 | A1 | 5/2025 | Janardhan et al. |
| 2025/0177692 | A1 | 6/2025 | Yee et al. |
| 2025/0195245 | A1 | 6/2025 | Lee et al. |
| 2025/0235221 | A1 | 7/2025 | Janardhan et al. |
| 2025/0255626 | A1 | 8/2025 | Childs et al. |
| 2025/0261956 | A1 | 8/2025 | Ray et al. |
| 2025/0281116 | A1 | 9/2025 | Strasser et al. |
| 2025/0325290 | A1 | 10/2025 | Brady et al. |
| 2025/0331876 | A1 | 10/2025 | Carney et al. |
| 2025/0352225 | A1 | 11/2025 | Nagireiter et al. |
| 2025/0359883 | A1 | 11/2025 | Kelly et al. |
| 2025/0387595 | A1 | 12/2025 | Yee et al. |
| 2026/0000863 | A1 | 1/2026 | Casey et al. |
| 2026/0007424 | A1 | 1/2026 | Brady et al. |
| 2026/0007425 | A1 | 1/2026 | Connolly |
| 2026/0026824 | A1 | 1/2026 | Childs et al. |
| 2026/0174449 | A1 | 6/2026 | Deville et al. |

FOREIGN PATENT DOCUMENTS

| | | | |
|---|---|---|---|
| CN | 105559854 | A | 5/2016 |
| CN | 110025834 | A | 7/2019 |
| CN | 211068270 | U | 7/2020 |
| CN | 111481262 | A | 8/2020 |
| CN | 111528983 | A | 8/2020 |
| CN | 112258514 | B | 11/2021 |
| DE | 4018736 | A1 | 1/1992 |
| EP | 1013287 | A2 | 6/2000 |
| EP | 3500191 | B1 | 9/2020 |
| EP | 3335647 | B1 | 1/2022 |
| EP | 4296949 | A1 | 12/2023 |
| JP | H0197951 | A | 4/1989 |
| JP | 2007117384 | A | 5/2007 |
| JP | 2009518134 | A | 5/2009 |
| JP | 2010505542 | A | 2/2010 |
| JP | 2010506653 | A | 3/2010 |
| JP | 2013154171 | A | 8/2013 |
| WO | WO89/05665 | A2 | 6/1989 |
| WO | WO94/016706 | A1 | 8/1994 |
| WO | WO2000/006224 | A1 | 2/2000 |
| WO | WO02/26289 | A1 | 4/2002 |
| WO | WO2003/084596 | A1 | 10/2003 |
| WO | WO2003/092537 | A2 | 11/2003 |
| WO | WO2004/000099 | A2 | 12/2003 |
| WO | WO2004/004546 | A2 | 1/2004 |
| WO | WO2004/043220 | A2 | 5/2004 |
| WO | WO2004/050144 | A2 | 6/2004 |
| WO | WO2004/093941 | A2 | 11/2004 |
| WO | WO2006/012242 | A2 | 2/2006 |
| WO | WO2006/012243 | A2 | 2/2006 |
| WO | WO2006/012244 | A2 | 2/2006 |
| WO | WO2006/086516 | A2 | 8/2006 |
| WO | WO2007/017876 | A2 | 2/2007 |
| WO | WO2007/041471 | A2 | 4/2007 |
| WO | WO2007/085025 | A2 | 7/2007 |
| WO | WO2008/124790 | A2 | 10/2008 |
| WO | WO2008/147760 | A1 | 12/2008 |
| WO | WO2009/035582 | A1 | 3/2009 |
| WO | WO2009/046439 | A2 | 4/2009 |
| WO | WO2009/062105 | A2 | 5/2009 |
| WO | WO2009/114826 | A2 | 9/2009 |
| WO | WO2009/131583 | A1 | 10/2009 |
| WO | WO2009/137800 | A2 | 11/2009 |
| WO | WO2009/155526 | A2 | 12/2009 |
| WO | WO2010/008834 | A2 | 1/2010 |
| WO | WO2010/085765 | A2 | 7/2010 |
| WO | WO2010/093692 | A2 | 8/2010 |
| WO | WO2010/117806 | A1 | 10/2010 |
| WO | WO2010/138919 | A2 | 12/2010 |
| WO | WO2011/022674 | A2 | 2/2011 |
| WO | WO2011/103096 | A2 | 8/2011 |
| WO | WO2011/103133 | A2 | 8/2011 |
| WO | WO2012/051433 | A2 | 4/2012 |
| WO | WO2013/119662 | A1 | 8/2013 |
| WO | WO2014/047626 | A2 | 3/2014 |
| WO | WO2015/196156 | A1 | 12/2015 |
| WO | WO2016/164930 | A1 | 10/2016 |
| WO | WO2017/070702 | A1 | 4/2017 |
| WO | WO2017/106877 | A1 | 6/2017 |
| WO | WO2017/161204 | A1 | 9/2017 |
| WO | WO2018/033401 | A1 | 2/2018 |
| WO | WO2018/080590 | A1 | 5/2018 |
| WO | WO2018/094050 | A2 | 5/2018 |
| WO | WO2019/050765 | A1 | 3/2019 |
| WO | WO2020/036809 | A1 | 2/2020 |
| WO | WO2020/181278 | A1 | 9/2020 |
| WO | WO2020/206366 | A1 | 10/2020 |
| WO | WO2021/076954 | A1 | 4/2021 |
| WO | WO2021/127202 | A1 | 6/2021 |
| WO | WO2021/178696 | A1 | 9/2021 |
| WO | WO2021/248042 | A1 | 12/2021 |
| WO | WO2022/032173 | A1 | 2/2022 |
| WO | WO2022/103848 | A1 | 5/2022 |
| WO | WO2022/109021 | A1 | 5/2022 |
| WO | WO2022/109034 | A1 | 5/2022 |
| WO | WO2022/120270 | A1 | 6/2022 |
| WO | WO2022/251678 | A1 | 12/2022 |

(56) References Cited

FOREIGN PATENT DOCUMENTS

| | | | |
|---|---|---|---|
| WO | WO2023/288268 | A1 | 1/2023 |
| WO | WO2023/049802 | A1 | 3/2023 |
| WO | WO2023/137341 | A1 | 7/2023 |
| WO | WO2023/147353 | A1 | 8/2023 |
| WO | WO2023/150730 | A2 | 8/2023 |
| WO | WO2023/154612 | A2 | 8/2023 |
| WO | WO2023/168415 | A1 | 9/2023 |
| WO | WO2023/178212 | A2 | 9/2023 |
| WO | WO2023/192925 | A2 | 10/2023 |
| WO | WO2023/215779 | A2 | 11/2023 |
| WO | WO2023/225676 | A2 | 11/2023 |
| WO | WO2023/239706 | A2 | 12/2023 |
| WO | WO2024/006482 | A2 | 1/2024 |
| WO | WO2024/016004 | A2 | 1/2024 |
| WO | WO2024/026493 | A2 | 2/2024 |
| WO | WO2024/044511 | A2 | 2/2024 |
| WO | WO2024/044671 | A1 | 2/2024 |
| WO | WO2024/044710 | A1 | 2/2024 |
| WO | WO2024/054988 | A2 | 3/2024 |
| WO | WO2024/059695 | A2 | 3/2024 |
| WO | WO2024/092054 | A2 | 5/2024 |
| WO | WO2024/092123 | A1 | 5/2024 |
| WO | WO2024/092278 | A1 | 5/2024 |
| WO | WO2024/097710 | A1 | 5/2024 |
| WO | WO2024/097711 | A1 | 5/2024 |
| WO | WO2024/103036 | A2 | 5/2024 |
| WO | WO2024/118919 | A1 | 6/2024 |
| WO | WO2024/225874 | A1 | 10/2024 |

OTHER PUBLICATIONS

Al-Jadda et al.; U.S. Appl. No. 19/123,732 entitled "Thrombus removal systems and methods for blood return and reconstituting removed blood clots," filed Apr. 23, 2025.

Gunning et al.; U.S. Appl. No. 19/123,712 entitled "Thrombus removal systems and associated methods," filed Apr. 23, 2025.

Al-Jadda et al.; U.S. Appl. No. 19/123,691 entitled "Thrombectomy system and method of removing thrombus," filed Apr. 23, 2025.

Al-Jadda et al.; U.S. Appl. No. 19/123,734 entitled "Thrombectomy system and method of removing thrombus," filed Apr. 23, 2025.

Dala et al.; U.S. Appl. No. 18/994,012 entitled "Thrombus removal systems and associated methods," filed Jan. 13, 2021.

Al-Jadda et al.; U.S. Appl. No. 19/106,171 entitled "Thrombus removal systems and associated methods," filed Feb. 24, 2025.

Al-Jadda et al.; U.S. Appl. No. 19/106,174 entitled "Contrast injection and visualization systems and methods for thrombus removal device," filed Feb. 24, 2025.

Gunning; U.S. Appl. No. 19/106,179 entitled "Thrombus removal systems and associated methods," filed Feb. 24, 2025.

Chen et al.; Formation of nanocrystalline AZ31B Mg alloys via cryogenic rotary swaging; Journal of Magnesium and Alloys; 11(5); pp. 1580-1591; May 1, 2023.

Eucker et al.; Phase plane analysis of left ventricular hemodynamics; Journal of Applied Physiology; 90(6); pp. 2238-2244; Jun. 1, 2001.

Saul; U.S. Appl. No. 18/867,656 entitled "Thrombus removal systems and associated methods," filed Nov. 20, 2024.

Anenberg et al.; Optogenetic stimulation of GABA neurons can decrease local neuronal activity while increasing cortical blood flow; Journal of Cerebral Blood Flow & Metabolism; 35(10); pp. 1579-1586; Oct. 2015.

Humbert et al.; 2022 ESC/ERS Guidelines for the diagnosis and treatment of pulmonary hypertension: Developed by the task force for the diagnosis and treatment of pulmonary hypertension of the European Society of Cardiology (ESC) and the European Respiratory Society (ERS); Endorsed by the International Society for Heart and Lung Transplantation (ISHLT) and the European Reference Network on rare respiratory diseases (ERN-LUNG); European heart journal; 43(38); pp. 3618-3731; Oct. 7, 2022.

Kondo et al.; Pulmonary hypertension: diagnosis, management, and treatment; Nagoya journal of medical science; 81(1); pp. 19-30; Feb. 2019.

Pigon et al.; In vitro comparison of Several Thrombus Removal Tools. Journal of Cardiovascular Development and Disease; 10(2); 69; Feb. 6, 2023.

Tanyildizi et al.; In vitro testing of a funnel-shaped tip catheter model to decrease clot migration during mechanical thrombectomy; Scientific Reports; 10(1); 7 pages; Jan. 20, 2020.

Weitzman et al.; A novel technology for large vessel recanalization; Innovations; 5(5); pp. 381-385; Sep. 2005.

Al-Jadda et al.; U.S. Appl. No. 18/568,656 entitled "Thrombus removal systems and associated meethods," filed Dec. 8, 2023.

Gunning et al.; U.S. Appl. No. 18/835,686 entitled "Thrombus removal systems and associated methods," filed Aug. 2, 2024.

Gunning et al.; U.S. Appl. No. 18/847,594 entitled "Thrombus removal systems and associated methods," filed Sep. 16, 2024.

Saul; U.S. Appl. No. 18/686,616 entitled "Thrombus removal systems and associated methods," filed Nov. 22, 2024.

Nicolini et al.; Histological analysis of thrombi retrieved after acute ischemic stroke from large vessel occlusion: from research to clinical practice; Vessel Plus; 2022; 6:2; 17 pages; Jan. 6, 2022.

Al-Jadda et al; U.S. Appl. No. 19/483,840 entitled "Thrombus removal system consoles and associated user interfaces," filed Nov. 12, 2025.

Illindala et al.; U.S. Appl. No. 19/512,638 entitled "Thrombus removal systems and methods," filed Feb. 19, 2026.

Illindala et al.; U.S. Appl. No. 19/514,320 entitled Thrombus removal systems and methods, filed Feb. 25, 2026.

* cited by examiner

Section C-C

Section B-B

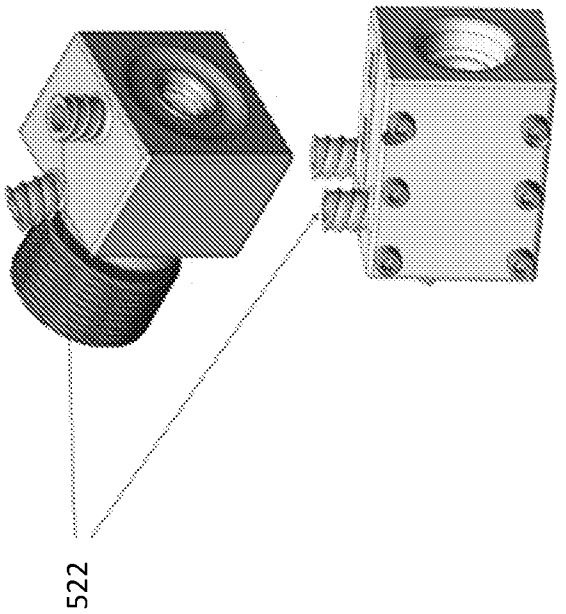
FIG. 5C
FIG. 5D
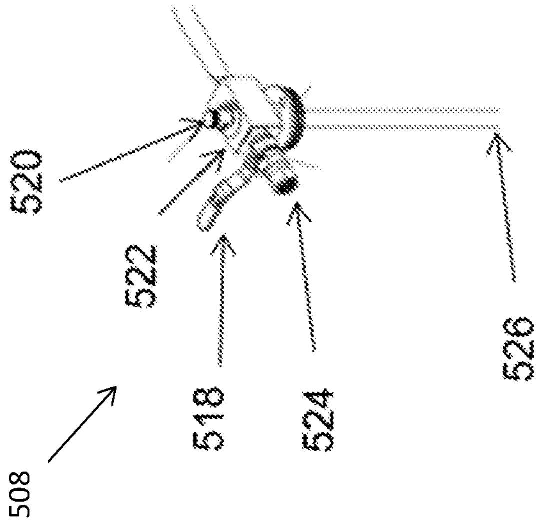
FIG. 5B

THROMBUS REMOVAL SYSTEMS AND ASSOCIATED METHODS

CLAIM OF PRIORITY

This application claims the benefit of U.S. Provisional Application No. 63/340,218, filed May 10, 2022, which is herein incorporated by reference in its entirety for all purposes.

INCORPORATION BY REFERENCE

All publications and patent applications mentioned in this specification are herein incorporated by reference to the same extent as if each individual publication or patent application was specifically and individually indicated to be incorporated by reference.

FIELD

The present technology generally relates to medical devices and, in particular, to systems including aspiration and fluid delivery mechanisms and associated methods for removing a thrombus from a mammalian blood vessel.

BACKGROUND

Thrombotic material may lead to a blockage in fluid flow within the vasculature of a mammal. Such blockages may occur in varied regions within the body, such as within the pulmonary system, peripheral vasculature, deep vasculature, or brain. Pulmonary embolisms typically arise when a thrombus originating from another part of the body (e.g., a vein in the pelvis or leg) becomes dislodged and travels to the lungs. Anticoagulation therapy is the current standard of care for treating pulmonary embolisms, but may not be effective in some patients. Additionally, conventional devices for removing thrombotic material may not be capable of navigating the tortuous vascular anatomy, may not be effective in removing thrombotic material, and/or may lack the ability to provide sensor data or other feedback to the clinician during the thrombectomy procedure. Existing thrombectomy devices operate based on simple aspiration which works sufficiently for certain clots but is largely ineffective for difficult, organized clots. Many patients presenting with deep vein thrombus (DVT) are left untreated as long as the risk of limb ischemia is low. In more urgent cases, they are treated with catheter-directed thrombolysis or lytic therapy to break up a clot over the course of many hours or days. More recently other tools like clot retrievers have been developed to treat DVT and pulmonary embolism (PE), but these tools are not being widely adopted because of their limited effectiveness and additional costs versus aspiration or the standard of case. Other recent developments focus on slicing or macerating the clot, but these mechanisms are designed to reduce the risk of the catheter clogging and do not address the problem of tough, large, organized clots. There remains the need for a device to address these and other problems with existing venous thrombectomy including, but not limited to, a fast, easy-to-use, and effective device for removing a variety of clot morphologies.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 5A-5D illustrate various views of a portion of a thrombus removal system including a distal portion of an elongated catheter configured in accordance with an embodiment of the present technology.

SUMMARY OF THE DISCLOSURE

Figure 1A:
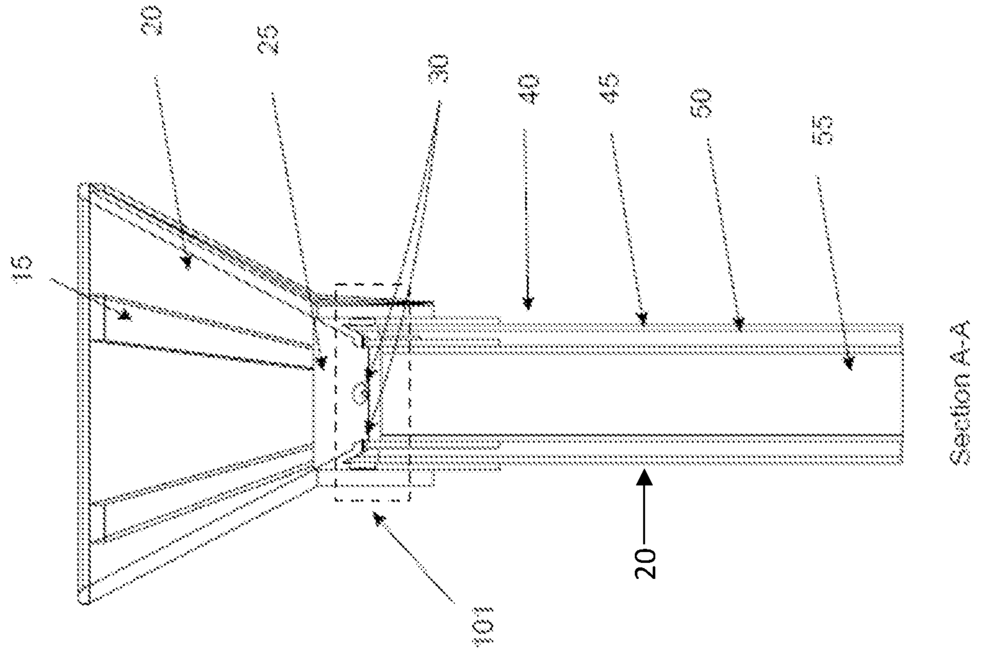
FIGS. 1-1L illustrate various views of a portion of a thrombus removal system including a distal portion of an elongated catheter configured in accordance with an embodiment of the present technology.

A thrombus removal is provided, comprising an elongate shaft comprising a working end, at least one fluid lumen in the elongate shaft, and two or more apertures disposed at or near the working end, the two or more apertures in fluid communication with the least one fluid lumen and configured to generate two or more fluid streams to mechanically fractionate a target thrombus.

A thrombectomy method is provided, comprising delivering a distal portion of an elongate catheter into proximity with a thrombus in a blood vessel; engaging the distal portion with the thrombus; and directing a particulate media towards the thrombus.

In one aspect, the method further comprises aspirating the thrombus out of the blood vessel.

In some aspects, directing the particulate media towards the thrombus further comprises combining the particulate media with a pressurized fluid.

In one aspect, the method further includes directing a fluid stream towards the thrombus. In one aspect, the fluid stream is directed towards the thrombus with one or more fluid stream apertures and the particulate media is directed towards the thrombus with one or more particulate media apertures. In other aspects, the fluid stream is carried within one or more fluid lumens in the elongate catheter and the particulate media is carried within one or more particulate media lumens in the elongate catheter.

In one aspect, the particulate media is an abrasive mixture. In another aspect, the particulate media comprises a salt. In some aspects, the particulate media comprises a sugar. In one aspect, the particulate media comprises a contrast media. In some aspects, the particulate media comprises lactated ringers. In another aspect, the particulate media comprises microparticles. In one aspect, the particulate media comprises microbeads. In other aspects, the particulate media includes a coating configured to reduce dissolution of the particulate media within the body. In some aspects, the particulate media the coating is a lipid coating.

In one aspect, directing the particulate media further comprises delivering a fluid to a mixing chamber; delivering the particulate media to the mixing chamber; and fluidizing the particulate media in the mixing chamber with the fluid.

In one aspect, introducing the distal portion is into the blood vessel in a low-profile configuration, and wherein the method further comprises expanding the distal portion into a deployed configuration.

In another aspect, the method includes directing the particulate media along at least two intersecting paths.

In some aspects, the blood vessel comprises a pulmonary artery.

A thrombectomy system is provided, comprising: an elongate shaft comprising a distal portion adapted to be inserted into a blood vessel; one or more lumens in the elongate shaft; a media source comprising a particulate media, the media source being fluidly coupled to the one or more lumens; and one or more ports disposed in the distal end and in fluid communication with the one or more lumens, the one or more ports being configured to direct a fluidized particulate media into the blood vessel towards a thrombus.

In one aspect, the system further comprises an aspiration lumen disposed in the elongate catheter; a vacuum source fluidly coupled to the aspiration lumen, the vacuum source being configured to aspirate the thrombus out of the blood vessel.

In one aspect, the system further comprises a fluid source comprising a fluid; a mixing chamber in fluid communication with the one or more lumens, the fluid source, and the media source, the mixing chamber being configured to combine the fluid with the particulate media.

In one aspect, the system further comprises a fluid source fluidly coupled to the one or more lumens, wherein the one or more ports are configured to direct a fluid stream into the blood vessel towards the thrombus.

In some aspects, the fluid stream is directed simultaneously with the fluidized particulate media.

In other aspects, the fluid stream is directed with one or more ports different than the one or ports that direct the fluidized particulate media.

In one aspect, the particulate media is an abrasive mixture. In another aspect, the particulate media comprises a salt. In some aspects, the particulate media comprises a sugar. In one aspect, the particulate media comprises a contrast media. In some aspects, the particulate media comprises lactated ringers. In another aspect, the particulate media comprises microparticles. In one aspect, the particulate media comprises microbeads. In other aspects, the particulate media includes a coating configured to reduce dissolution of the particulate media within the body. In some aspects, the particulate media the coating is a lipid coating.

In some aspects, the one or more ports are configured to direct the fluidized particulate media along at least two intersecting paths.

In other aspects, the distal portion further comprises a funnel.

In one aspect, the funnel is expandable.

DETAILED DESCRIPTION

This application is related to disclosure in International Application No. PCT/US2021/020915, filed Mar. 4, 2021 (the '915 application), and International Application No. PCT/US2022/033024, filed Jun. 10, 2022 (the '024 application), the disclosures of which are incorporated by reference herein for all purposes. The '915 and '024 applications describe general mechanisms for capturing and removing a clot. By example, multiple fluid streams are directed toward the clot to fragment the material.

The present technology is generally directed to thrombus removal systems and associated methods. A system configured in accordance with an embodiment of the present technology can include, for example, an elongated catheter having a distal portion configured to be positioned within a blood vessel of the patient, a proximal portion configured to be external to the patient, a fluid delivery mechanism configured to fragment the thrombus with pressurized fluid, an aspiration mechanism configured to aspirate the fragments of the thrombus, and one or more lumens extending at least partially from the proximal portion to the distal portion.

The terminology used in the description presented below is intended to be interpreted in its broadest reasonable manner, even though it is being used in conjunction with a detailed description of certain specific embodiments of the present technology. Certain terms may even be emphasized below; however, any terminology intended to be interpreted in any restricted manner will be overtly and specifically defined as such in this Detailed Description section. Additionally, the present technology can include other embodiments that are within the scope of the examples but are not described in detail with respect to the figures.

Reference throughout this specification to "one embodiment" or "an embodiment" means that a particular feature, structure, or characteristic described in connection with the embodiment is included in at least one embodiment of the present technology. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

Reference throughout this specification to relative terms such as, for example, "generally," "approximately," and "about" are used herein to mean the stated value plus or minus 10%.

Although some embodiments herein are described in terms of thrombus removal, it will be appreciated that the present technology can be used and/or modified to remove other types of emboli that may occlude a blood vessel, such as fat, tissue, or a foreign substance. Additionally, although some embodiments herein are described in the context of thrombus removal from a pulmonary artery (e.g., pulmonary embolectomy), the technology may be applied to removal of thrombi and/or emboli from other portions of the vasculature (e.g., in neurovascular, coronary, or peripheral applications). Moreover, although some embodiments are discussed in terms of maceration of a thrombus with a fluid, the present technology can be adapted for use with other techniques (e.g., ultrasonic, mechanical, enzymatic, etc.) for breaking up a thrombus into smaller fragments.

The headings provided herein are for convenience only and do not interpret the scope or meaning of the claimed present technology.

Systems for Thrombus Removal

As provided above, the present technology is generally directed to thrombus removal systems. Such systems include an elongated catheter having a distal portion positionable within a blood vessel of the patient (e.g., an artery or vein), a proximal portion positionable outside the patient's body, a fluid delivery mechanism configured to fragment the thrombus with pressurized fluid, an aspiration mechanism configured to aspirate the fragments of the thrombus, and one or more lumens extending at least partially from the proximal portion to the distal portion. In some embodiments, the systems herein are configured to engage a thrombus in a patient's blood vessel, break the thrombus into small fragments, and aspirate the fragments out of the patient's body. The pressurized fluid streams (e.g., jets) function to cut or macerate thrombus, before, during, and/or after at least a portion of the thrombus has entered the aspiration lumen or a funnel of the system. Fragmentation helps to prevent clogging of the aspiration lumen and allows the thrombus removal system to macerate large, firm clots that otherwise could not be aspirated. As used herein, "thrombus" and "embolism" are used somewhat interchangeably in various respects. It should be appreciated that while the description may refer to removal of "thrombus," this should be understood to encompass removal of thrombus fragments and other emboli as provided herein.

According to embodiments of the present technology, a fluid delivery mechanism can provide a plurality of fluid streams (e.g., jets) to fluid apertures of the thrombus removal system for macerating, cutting, fragmenting, pulverizing and/or urging thrombus to be removed from a proximal portion of the thrombus removal system. The thrombus removal system can include an aspiration lumen extending at least partially from the proximal portion to the distal portion of the thrombus removal system that is adapted for fluid communication with an aspiration pump (e.g., vacuum source). In operation, the aspiration pump may generate a volume of lower pressure within the aspiration lumen near the proximal portion of the thrombus removal system, urging aspiration of thrombus from the distal portion.

Figure 1:
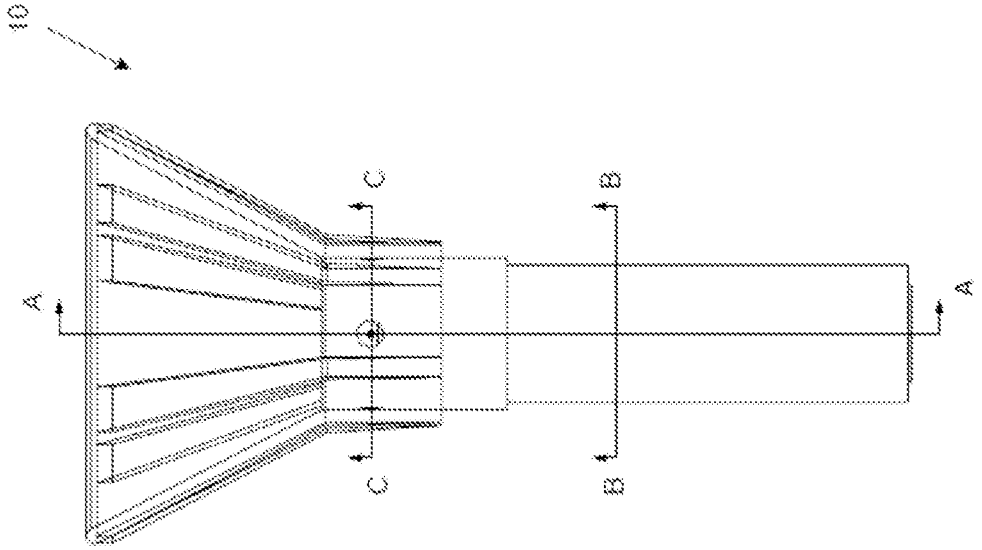

FIG. 1 illustrates a distal portion 10 of a thrombus removal system according to an embodiment of the present technology. FIG. 1A Section A-A illustrates an elevation sectional view of the distal portion. The example section A-A in FIG. 1A depicts a funnel 20 that is positioned at the distal end of the distal portion 10, the funnel adapted to engage with thrombus within a blood vessel and/or a tissue (e.g., vessel) wall to aid in thrombus fragmentation and/or removal. The funnel can have a variety of shapes and constructions as would be understood by one of skill from the description herein. The thrombus removal system may be delivered through a sheath to a thrombus site in a blood vessel with funnel 20 in a compressed configuration. Funnel 20 may self-expand as it is advanced out of the sheath and/or as the sheath is retracted from the funnel.

The example section A-A in FIG. 1A depicts a double walled thrombus removal device construction having a catheter 22 extending proximally from funnel 20 with an outer wall/tube 40 and an inner wall/tube 50. An aspiration lumen 55 is formed by the inner wall 50 and is centrally located. Aspiration lumen 55 communicates with a vacuum source, as described below. A generally annular volume forms at least one fluid lumen 45 between the outer wall 40 and the inner wall 50. The fluid lumen 45 is adapted for fluid communication with a fluid delivery mechanism and/or a particulate media source, as described below. One or more apertures (e.g., nozzles, orifices, or ports) 30 are positioned in the thrombus removal system to be in fluid communication with the fluid lumen 45 and an irrigation manifold 25 at the base of funnel 20. In operation, the ports 30 are adapted to direct (e.g., pressurized) fluid toward thrombus material that is engaged with the distal portion 10 of the thrombus removal system to macerate, fragment, or cut the thrombus material. As will be described below, in some embodiments the fluid can include or comprise particulate media. Aspiration lumen 55 pulls thrombus material along with fluid from ports 30 and blood from the blood vessel proximally to a receptacle outside of the patient, as described below.

In various embodiments, the system can have an average flow velocity within the fluid lumen of up to 20 m/s to achieve consistent and successful aspiration of clots. In some embodiments, the fluid source itself can be delivered in a pulsed sequence or a preprogrammed sequence that includes some combination of pulsatile flow and constant flow to deliver fluid to the jets. In these embodiments, while the average pulsed fluid velocity may be up to 20 m/s, the peak fluid velocity in the lumen may be up to 30 m/s or more during the pulsing of the fluid source. In some embodiments, the jets or apertures are no smaller than 0.0100" or even as small as 0.008" to avoid undesirable spraying of fluid. In some embodiments, the system can have a minimum vacuum or aspiration pressure of 1 in Hg to 2 in Hg absolute, to remove target clots after they have been macerated or broken up with the jets described above.

The thrombus removal system can be sized and configured to access and remove thrombi in various locations or vessels within a patient's body. It should be understood that while the dimensions of the system may vary depending on the target location, generally similar features and components described herein may be implemented in the thrombus removal system regardless of the application. For example, a thrombus removal system configured to remove pulmonary embolism (PE) from a patient may have an outer wall/tube with a size of approximately 11-13 Fr, or preferably 12 Fr, and an inner wall/tube with a size of 7-9 Fr, or preferably 8 Fr. A deep vein thrombosis (DVT) device, on the other hand, may have an outer wall/tube with a size of approximately 9-11 Fr, or preferably 10 Fr, and an inner wall/tube with a size of 6-9 Fr, or preferably 7.5 Fr. Applications are further provided for ischemic stroke and peripheral embolism applications.

Figure 1B:
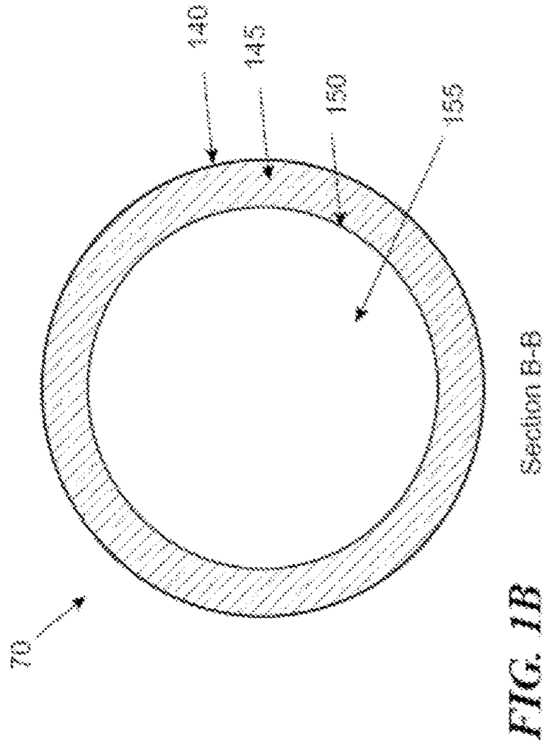
Figure 1C:
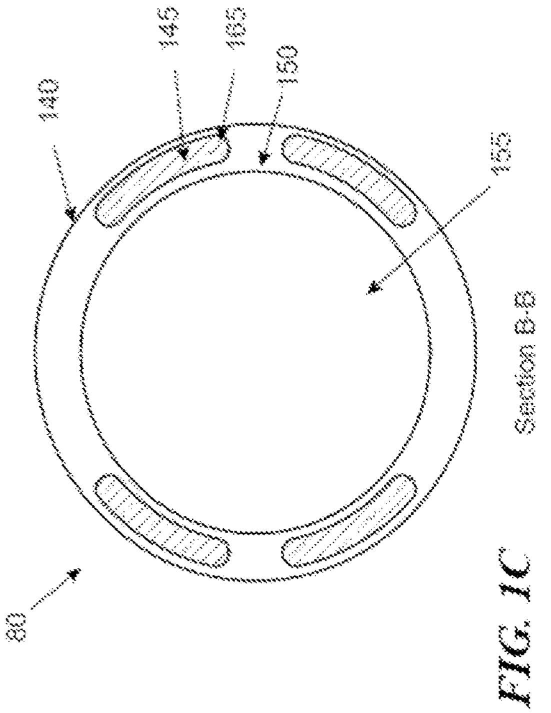

Section B-B of FIG. 1B illustrates in plain view a portion of the thrombus removal system that is proximal to the funnel and irrigation manifold. Section B-B depicts an outer wall 140, an inner wall 150, an aspiration lumen 155 and a fluid lumen 145. In some embodiments, in cross-section the aspiration lumen 155 is generally circular and the fluid lumen 145 is generally annular in shape (e.g., cross-section 70). It will be appreciated that alternative constructions and/or arrangements of the inner wall 150 and the outer wall 140 produce variations in cross-sectional shape of the aspiration and fluid lumens 155 and 145. For example, the inner wall 150 can be shaped to form an aspiration lumen 155 that, in cross-section, is generally oval, circular, rectilinear, square, pentagonal, or hexagonal. The inner and outer walls 150 and 140 can be shaped and arranged to form a fluid lumen 145 that, in cross-section, is generally crescent-shaped, diamond shaped, or irregularly shaped. For example, referring to FIG. 1C Section B-B, the region between the inner wall 150 and the outer wall 140 can include one or more wall structures 165 that form respective fluid lumens 145 (e.g., as in cross-section 80). The wall structures 165 can be formed by lamination between the outer and inner walls 140 and 150, or by a multi-lumen extrusion that forms a plurality of the wall structures.

Figure 1D:
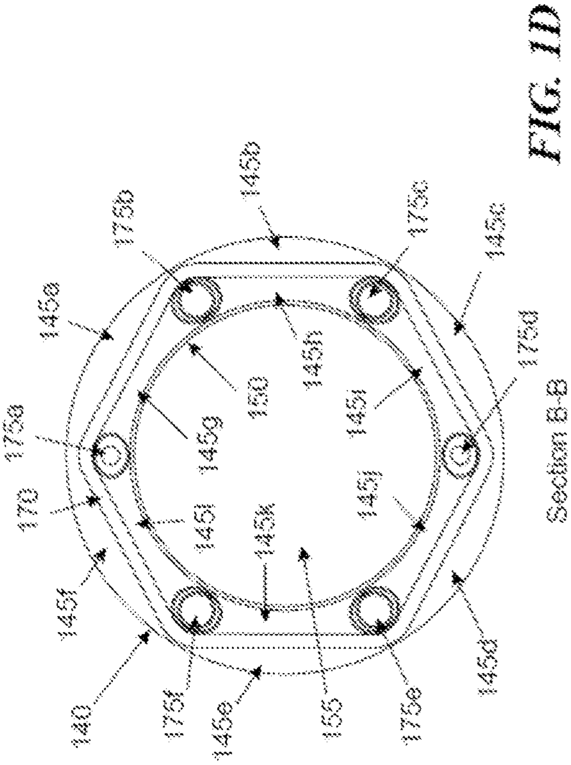

Section B-B of FIGS. 1D-1H illustrate additional examples of a portion of the thrombus removal system that is proximal to the funnel and irrigation manifold. Similar to the embodiments described above, the portion in these examples can include an outer wall 140, an inner wall 150, and an aspiration lumen 155. Additionally, the illustrated portion of the thrombus removal system can include a middle wall 170 disposed between the outer wall 140 and the inner wall 150. The middle wall 170 enables further segmentation of the annular space between the inner wall and outer wall into a plurality of distinct fluid lumens and/or auxiliary lumens. For example, referring to FIG. 1D, the middle wall can be generally hexagon shaped, and the annular space can include a plurality of fluid lumens 145*a*-141 and a plurality of auxiliary lumens 175*a*-175*f*. As shown in FIG. 1D, the fluid lumens can be formed by some combination of the outer wall 140 and the middle wall 170, or between the middle wall 170, the inner wall 150, and two of the auxiliary lumens. For example, fluid lumen 145*a* is formed in the space between outer wall 140 and middle wall 170. However, fluid lumen 145*g* is formed in the space between middle wall 170, inner wall 150, auxiliary lumen 175*a*, and auxiliary lumen 175*b*. Generally, the fluid lumens are configured to carry a flow of fluid such as saline from a saline source of the system to one or more ports/apertures/orifices of the system. The fluid lumens can also carry a fluid mixed with a particulate media, or a separate particulate media from the irrigation/jetting fluid. The auxiliary lumens can be configured for a number of functions. In some embodiments, the auxiliary lumens can be coupled to the fluid/saline source and to the apertures to be used as additional fluid lumens. In other embodiments, the auxiliary lumens can be configured as steering ports and can include a guide wire or steering wire within the lumen for steering of the thrombus removal system. In some embodiments, the auxiliary lumens can be dedicated for carrying a particulate media for delivering to clots. For example, the fluid lumens can carry irrigation or jetting fluid to fluid apertures, and the auxiliary lumens can carry particulate media to particulate media apertures. The fluid/saline jets can work in combination or independently with particulate media apertures. Additionally, in other embodiments, the auxiliary lumens can be configured to carry electrical, mechanical, or fluid connections to one or more sensors. For example, the system may include one or more electrical, optical, or fluid based sensors disposed along any length of the system. The sensors can be used during therapy to provide feedback for the system (e.g., sensors can be used to detect clogs to initiate a clog removal protocol, or to determine the proper therapy mode based on sensor feedback such as jet pulse sequences, aspiration sequences, etc.). The auxiliary ports can therefore be used to connect to the sensors, e.g., by electrical connection, optical connection, mechanical/wire connection, and/or fluid connection. It is also contemplated that the fluid and auxiliary lumens can be configured to carry and deliver other fluids, such as thrombolytics or radio-opaque contrast injections to the target tissue site during treatment.

It should be understood that in some embodiments, all the fluid lumens are fluidly connected to all of the jets or apertures of the thrombus removal device. Therefore, when a flow of fluid and/or particulate media is delivered from the fluid lumen(s) to the jets, all jets are activated with a jet of fluid at once. However, it should also be understood that in some embodiments, the fluid lumens are separate or distinct, and these distinct fluid lumens may be fluidly coupled to one or more jets but not to all jets of the device. In these embodiments, a subset of the jets can be controlled by delivering fluid only to the fluid lumens that are coupled to that subset of jets. This enables additional functionality in the device, in which specific jets can be activated in a user defined or predetermined order. For example, specific jets could deliver fluid or saline jet streams into a clot, and other jets could deliver particulate media into a clot.

In various embodiments, the fluid pressure is generated at the pump (in the console or handle). The fluid is accelerated as it exits the ports at the distal end and is directed to the target clot. In this way a wider variety of cost-effective components can be used to form the catheter while still maintaining a highly-effective device for clot removal. Additional details are provided below.

Figure 1E:
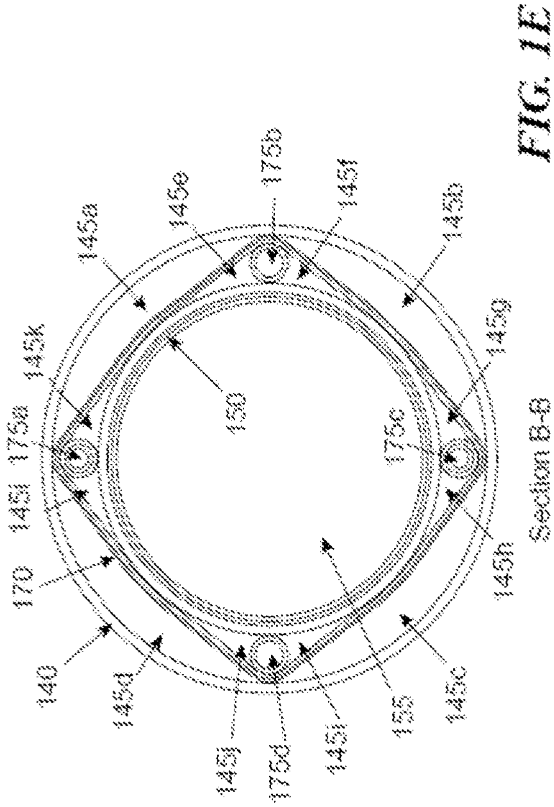
Figure 1F:
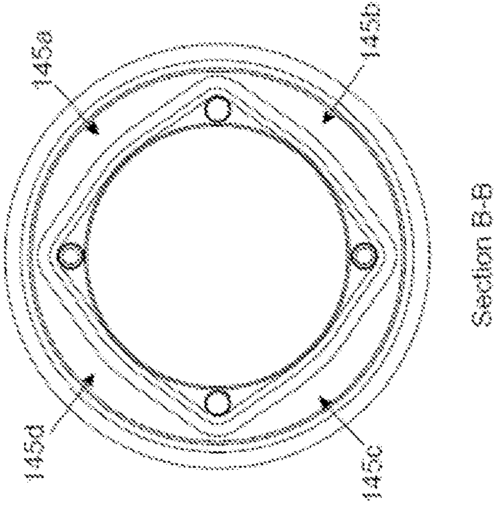

Section B-B of FIG. 1E illustrates another embodiment of the portion of the thrombus removal system that is proximal to the funnel and irrigation manifold. Similar to the embodiment of FIG. 1D, this embodiment also includes a middle wall 170. However, the middle wall in this example is generally square shaped, facilitating the formation of fluid lumens 145*a*-145*k* and auxiliary lumens 175*a*-175*d*. The example illustrated in section B-B of FIG. 1F is similar to that of the embodiment of FIG. 1E, however this embodiment includes only fluid lumens 145*a*-145*d*. The fluid lumens 145*e*-145*k* from the embodiment of FIG. 1E are not used as fluid lumens in this embodiment. They can be, for example, empty lumens, vacuum, filled with an insulative material, and/or filled with a radio-opaque material or any other material that may help visualize the thrombus removal system during therapy. The embodiment 1F includes the same four auxiliary reports as illustrated and described in the embodiment of FIG. 1E.

Figure 1G:
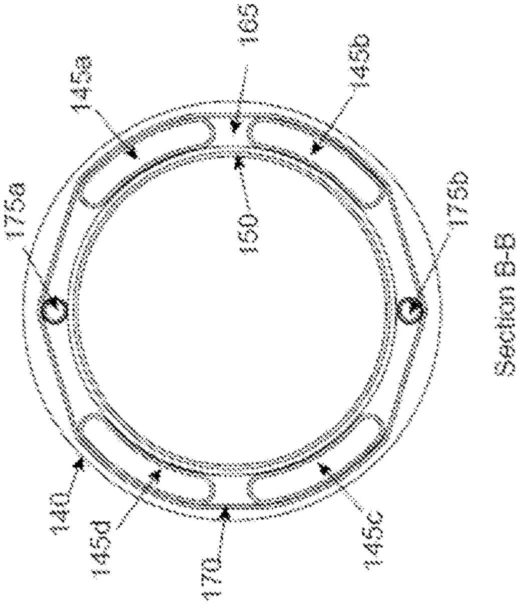

Section B-B of FIG. 1G illustrates another example of a portion of the thrombus removal system that is proximal to the funnel and irrigation manifold. Similar to the embodiments described above, the illustrated portion of the thrombus removal system can include a middle wall 170 disposed between the outer wall 140 and the inner wall 150. However, this embodiment includes four distinct fluid lumens 145*a*-145*d* formed by wall structures 165. As with the embodiment of FIG. 1C, the wall structures 165 can be formed by lamination between the outer and inner walls 140 and 150, or by a multi-lumen extrusion that forms a plurality of the wall structures. As shown, this embodiment can include a pair of auxiliary lumens 175*a* and 175*b*, which can be used, for example, for steering or for sensor connections as described above.

Figure 1H:
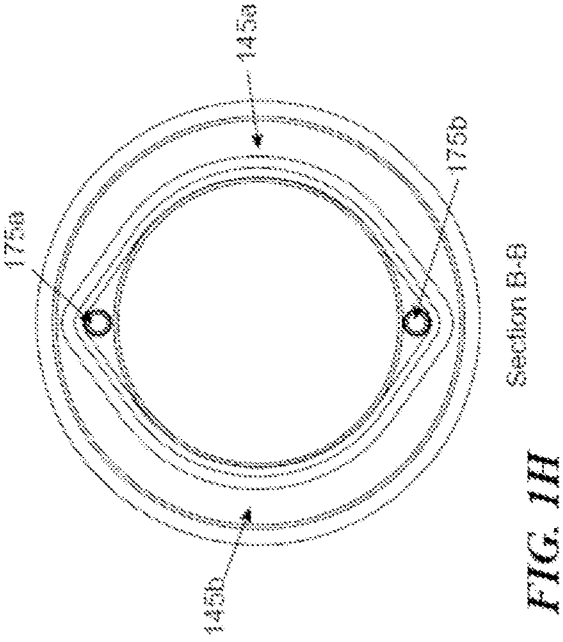
Figure 1I:
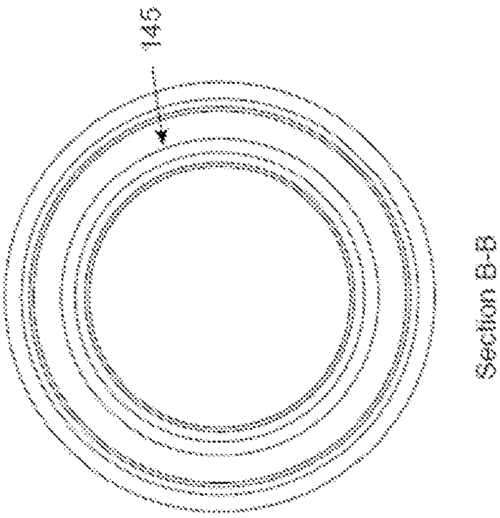

Section B-B of FIG. 1H is another similar embodiment in which the middle wall and outer wall can be used to form fluid lumens 145*a* and 145*b*. Auxiliary lumens 175*a* and 175*b* can be formed in the space between the middle wall and the inner wall. It should be understood that the middle wall can contact the outer wall to create independent fluid lumens 145*a* and 145*b*. However, in other embodiments, it should be understood that the middle wall may not contact the outer wall, which would facilitate a single annular fluid lumen, such as is shown by fluid lumen 145 in Section B-B of FIG. 1I. In another embodiment, as shown in Section B-B of FIG. 1J, the inner wall 150 and the outer wall 140 may not be concentric, which facilitates formation of an annular space and/or fluid lumen 145 that is thicker or wider on one side of the device relative to the other side. As shown in FIG. 1J, a distance between the exemplary outer wall 140 and inner wall at the top (e.g., 12 o'clock) portion of the device is larger than a distance between the outer wall and inner wall at the bottom (e.g., 6 o'clock) portion of the device.

Figure 1K:
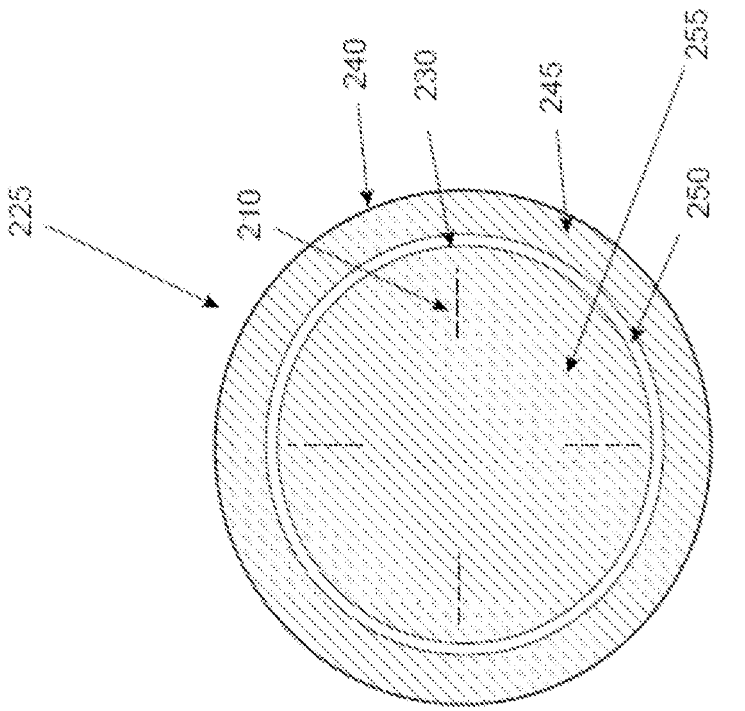
Figure 1J:
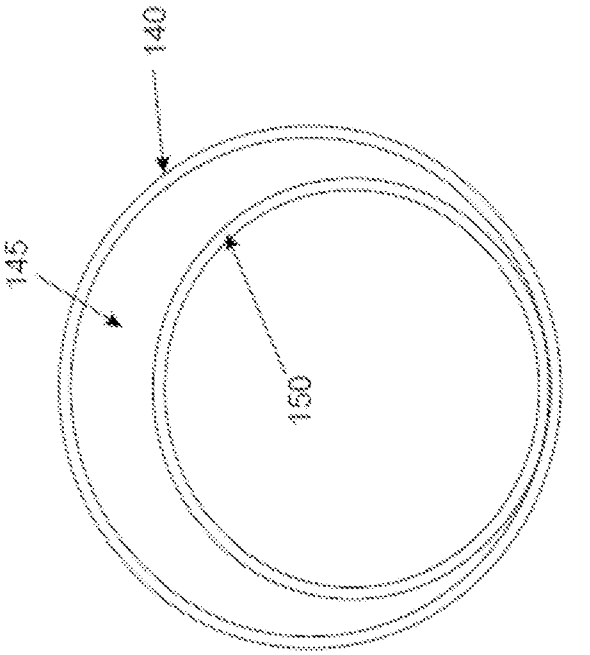
Figure 1L:
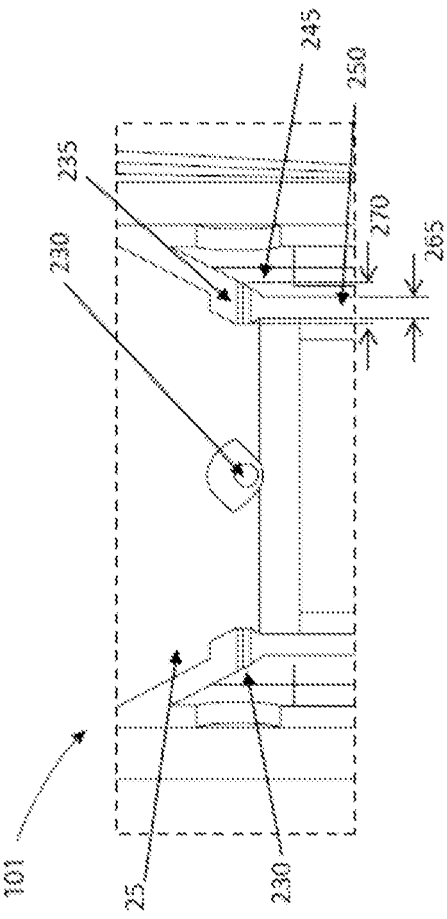
Figure 2A:
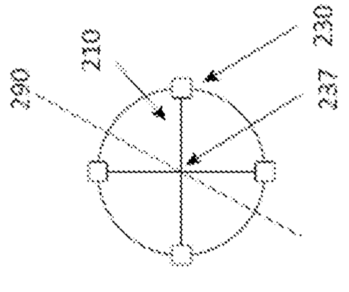
FIGS. 2A-2E illustrate plan views of various configurations of irrigation ports and fluid streams of a thrombus removal system according to embodiments of the present technology.
Figure 2B:
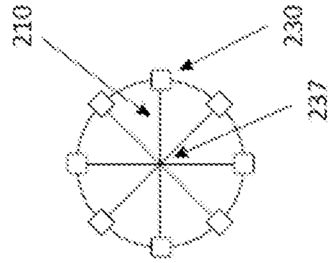
Figure 2C:
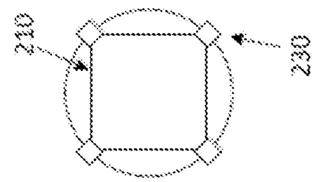
Figure 2D:
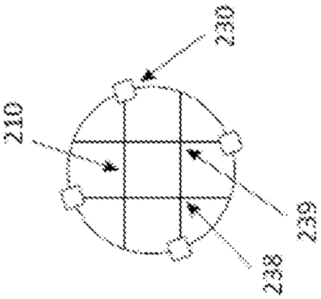
Figure 2E:
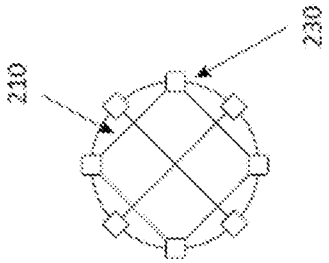
Figures 3A, 3B, 3C, 3D, 3E, 3F, 3G, 3H:
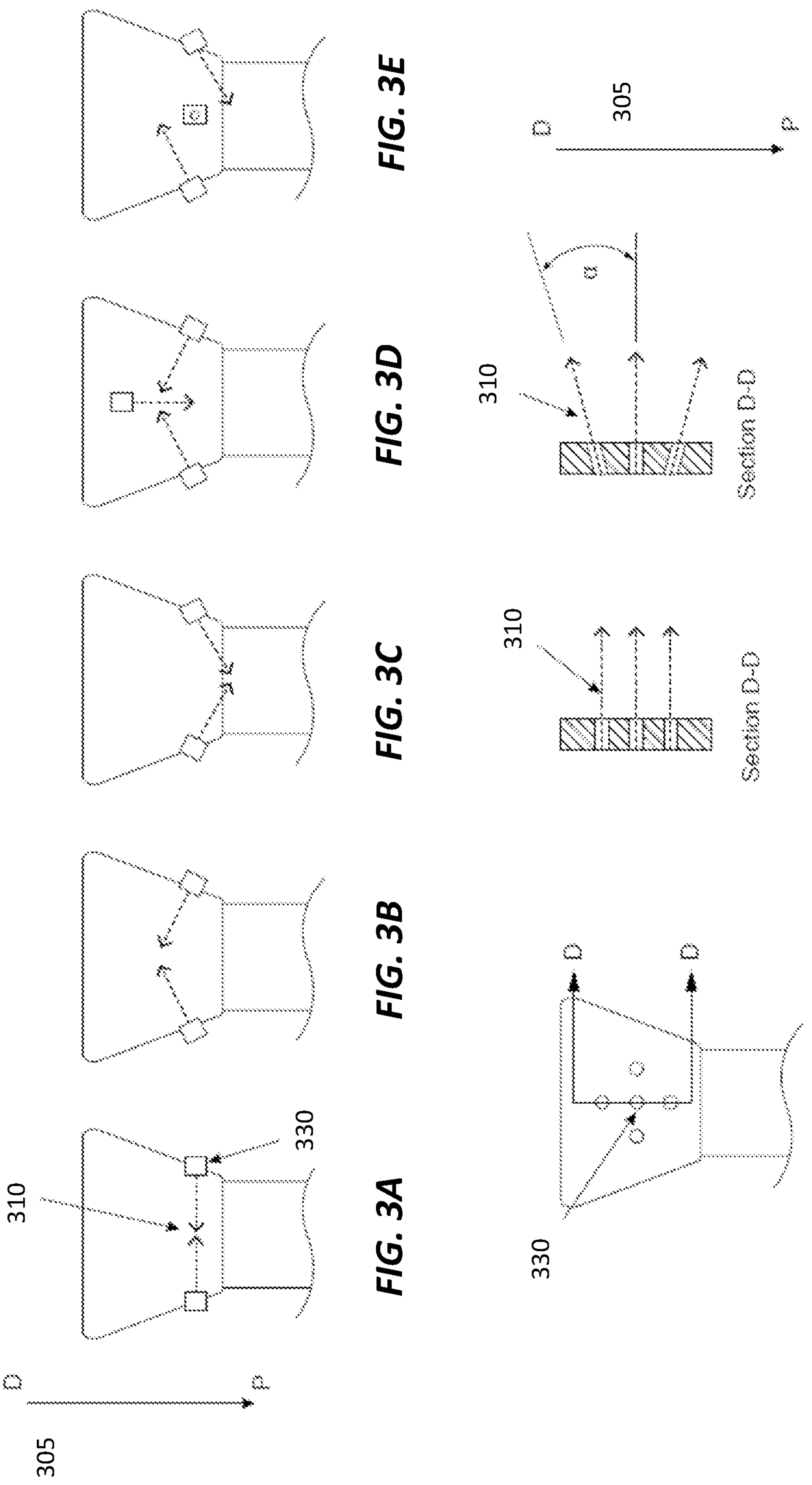
FIGS. 3A-3H illustrate an elevation view of various configurations of irrigation ports and fluid streams of a thrombus removal system according to embodiments of the present technology.

Section C-C of FIG. 1K illustrates in plain view a portion of the thrombus removal system comprising an irrigation manifold 225. Section C-C depicts an outer wall 240, an inner wall 250, a fluid lumen 245, an aspiration lumen 255, and ports 230 for directing respective fluid streams 210.

Detail View 101 of FIG. IL illustrates a section view in elevation of a portion of the irrigation manifold 25 at the base of the funnel that includes a plurality of ports 230 that are formed within an inner wall 250. In some embodiments, a thickness of one or more walls of the thrombus removal system may be varied along its axial length and/or its circumference. As shown in Detail View 101, inner wall 250 has a first thickness 265 in a region 250 that is proximal to the irrigation manifold 25, and a second thickness 270 in a region 235 that includes the ports 230. In some embodiments, the second thickness 270 is greater than the first thickness 265. The first thickness 265 can correspond to a general wall thickness of the inner wall 50 and/or of the outer wall 40, which can be from about 0.10 mm to about 0.60 mm, or any value within the aforementioned range. The second thickness 270 can be from about 0.20 mm to about 0.70 mm, from about 0.70 mm to about 0.90 mm, or from about 0.90 mm to about 1.20 mm. The second thickness 270 can be any value within the aforementioned range. The dimension of the second thickness 270 can be selected to provide a fluid path through the ports 230 that produces a generally laminar flow for a fluid stream that is directed therethrough, when the fluid delivery mechanism supplies fluid via the fluid lumen 245 at a typical operating pressure. Such operating pressure can be from about 10 psi to about 60 psi, from about 60 psi to about 100 psi, or from about 100 psi to about 150 psi. The operating pressure of the fluid delivery mechanism can be any value within the aforementioned range of values. In some embodiments, the fluid delivery mechanism is operated in a high pressure mode, having a pressure from about 150 psi to about 250 psi, from about 250 psi to about 350 psi, from about 350 psi to about 425 psi, or from about 425 psi to about 500 psi. The operating pressure of the fluid delivery mechanism in the high pressure mode can be any value within the aforementioned range of values.

The manifold is configured to increase a fluid pressure and/or flow rate of the fluid. When fluid is provided by the fluid delivery mechanism to the fluid lumen(s) at a first pressure and/or a first flow rate, the manifold is configured to increase the pressure of the fluid to a second pressure and/or is configured to increase the flow rate of the fluid to a second flow rate. The second pressure and/or second fluid rate can be higher than the first pressure and/or first flow rate. As a result, the manifold can be configured to increase the relatively low operating pressures and/or flow rates generated by the fluid delivery mechanism to the relatively high pressures and/or high flow rates generated by the ports/fluid streams.

In some embodiments, a profile (cross-sectional dimension) of a port 230 varies along its length (e.g., is non-cylindrical). A variation in the cross-sectional dimension of the port may alter and/or adjust a characteristic of fluid flow along the port 230. For example, a reduction in cross-sectional dimension may accelerate a flow of fluid through the port 230 (for a given volume of fluid). In some embodiments, a port 230 may be conical along its length (e.g., tapered), such that its smallest dimension is positioned at the distal end of the port 230, where distal is with respect to a direction of fluid flow.

In some embodiments, the port 230 is formed to direct the fluid flow along a selected path. FIGS. 2A-2E illustrate various embodiments of arrangements of ports 230 for directing respective fluid streams 210. In some embodiments, such as those shown in FIGS. 2A and 2B, at least two ports 230 are arranged to produce (e.g., respective) fluid streams 210 that intersect at an intersection region 237 of the thrombus removal system. An intersection region 237 can be a region of increased fluid momentum and/or energy transfer, which multiply with respect to individual fluid streams that are not directed to combine at the intersection. The increased fluid momentum and/or energy transfer at an intersection may advantageously fragment thrombus more efficiently and/or quickly. As described above, in some embodiments, the fluid streams can be configured to accelerate and cause cavitation and/or other effects to further add to breaking up of the target clot. In some embodiments, an intersection region can be formed from at least 2, at least 3, at least 4, at least 5, at least 6, at least 7, at least 8, at least 9, or at least 10 fluid streams 210. An intersection region can be generally near a central axis 290 of the thrombus removal system (e.g., 237), or away from the central axis (e.g., 238 and 239 in the embodiment of FIG. 2D). In some embodiments, at least two intersection regions (e.g., 238 and 239) are formed. In some embodiments, one or more ports 230 are arranged to direct a fluid stream 210 along an oblique angle with respect to the central axis of the thrombus removal system. An operating pressure of the fluid delivery mechanism may be selected to approach a minimum targeted fluid velocity for a fluid stream 210 that is delivered from a port 230. The targeted fluid velocity for a fluid stream 210 can be about 5 meters/second (m/s), about 8 m/s, about 10 m/s, about 12 m/s, or about 15 m/s. Additionally, the targeted fluid velocities in some embodiments can be in the range above 15 m/s to up to 150 m/s. At these higher velocities (e.g., above 15 m/s, or alternatively above 20 m/s), the fluid streams may be configured to generate cavitation in a target thrombus or tissue. It has been found that with fluid exiting from the ports to these flow rates a cavitation effect can be created in the focal area of the intersecting or colliding fluid streams, or additionally at a boundary of one or more of the fluid streams. While the exact specifications may change based on the catheter size, in general, at least one of the fluid streams should be accelerated to such a high velocity to create cavitation as described in detail below. The targeted fluid velocity for fluid stream 210 can be any value within the range of aforementioned values. In some embodiments, at least two ports 230 are adapted to deliver respective fluid streams at different fluid velocities (i.e., speed and direction), for a given pressure of the fluid delivery mechanism. In some embodiments, at least two ports 230 are adapted to deliver respective fluid streams at the substantially the same fluid velocities, for a given pressure of the fluid delivery mechanism. In some embodiments, one port is adapted to deliver fluid at high velocity and the respective one or more other ports is adapted to deliver fluid at relatively lower velocities. Advantageously, an increased cross-sectional area of the fluid lumen 145 reduces a required operating pressure of the fluid delivery mechanism to achieve a targeted fluid velocity of the fluid streams.

In some embodiments, the fluid streams are configured to create angular momentum that is imparted to a thrombus. In some examples, angular momentum is imparted on the thrombus by application of a) at least one fluid stream 210 that is directed at an oblique angle from a port 230, and/or b) at least two fluid streams 210 that have different fluid velocities. For example, fluid streams that cross near each other but do not necessarily intersect may create a "swirl" or rotational energy on the clot material. Advantageously, angular momentum produced in a thrombus may impart a (e.g., centrifugal) force that assists in fragmentation and removal of the thrombus. Rotating of the clot may enhance delivery of the clot material to the jets. By example, with a large, amorphous clot the soft material may be easily aspirated or broken up by the fluid streams whereas tough fibrin may be positioned away from the fluid streams. Rotating or swirling of the clot moves the material around so the harder clot material is presented to the jets. The swirling may also further break up the clot as it is banged inside the funnel.

FIGS. 3A-3H depict various configurations of fluid streams 310 that are directed from respective ports 330. A fluid stream 310 can be directed along a path that is substantially orthogonal, proximal, and/or distal to the flow axis 305. In some embodiments, at least two fluid streams are directed in different directions with respect to the flow axis 305. In some embodiments, at least two fluid streams are directed in a same direction (e.g., proximally) with respect to the flow axis 305. In some embodiments, at least a first fluid stream is directed orthogonally, at least a second fluid stream is directed proximally, and at least a third fluid stream is directed distally with respect to the flow axis 305. An angle α may characterize an angle that a fluid stream 310 is directed with respect to an axis that is orthogonal to the flow axis 305 (e.g., as shown in section D-D of FIGS. 3G and 3H). An intersection region of fluid streams can be within an interior portion of the thrombus removal system, and/or exterior (e.g., distal) to the thrombus removal system. In some embodiments, a fluid stream that is directed by a port 330 in a nominal direction (e.g., distally) is deflected along an altered path (e.g., proximally) by (e.g., suction) pressure generated by the aspiration mechanism during operation.

Figure 4A:
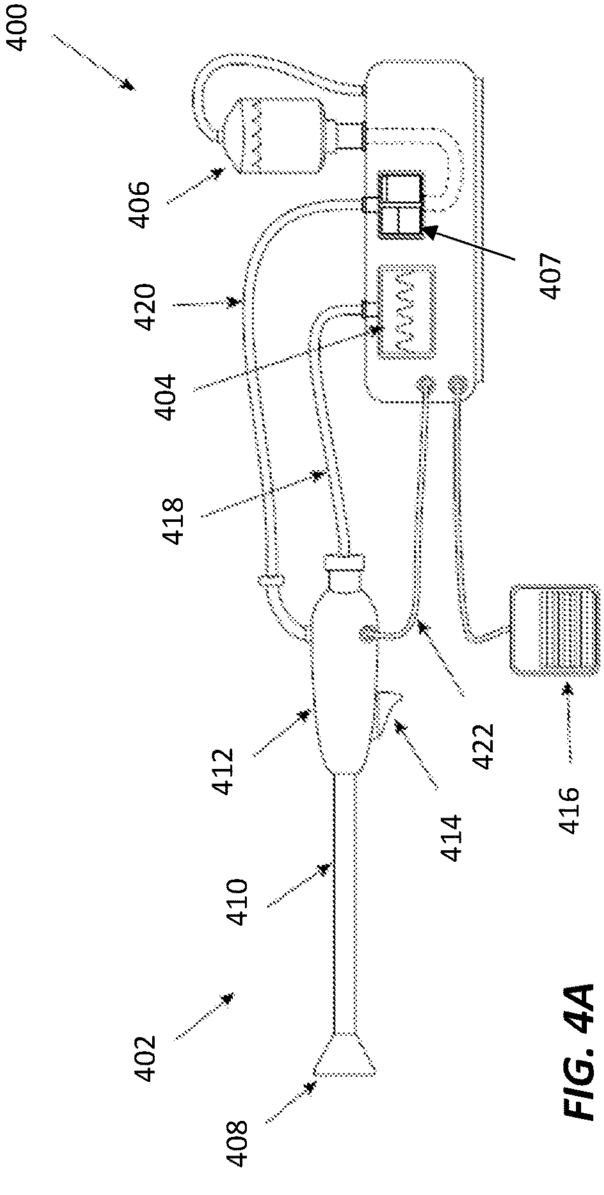
FIGS. 4A-4C illustrate various embodiments of a thrombus removal system including a saline source, an aspiration system, and one or more controls for controlling irrigation and/or aspiration of the system.
Figure 4B:
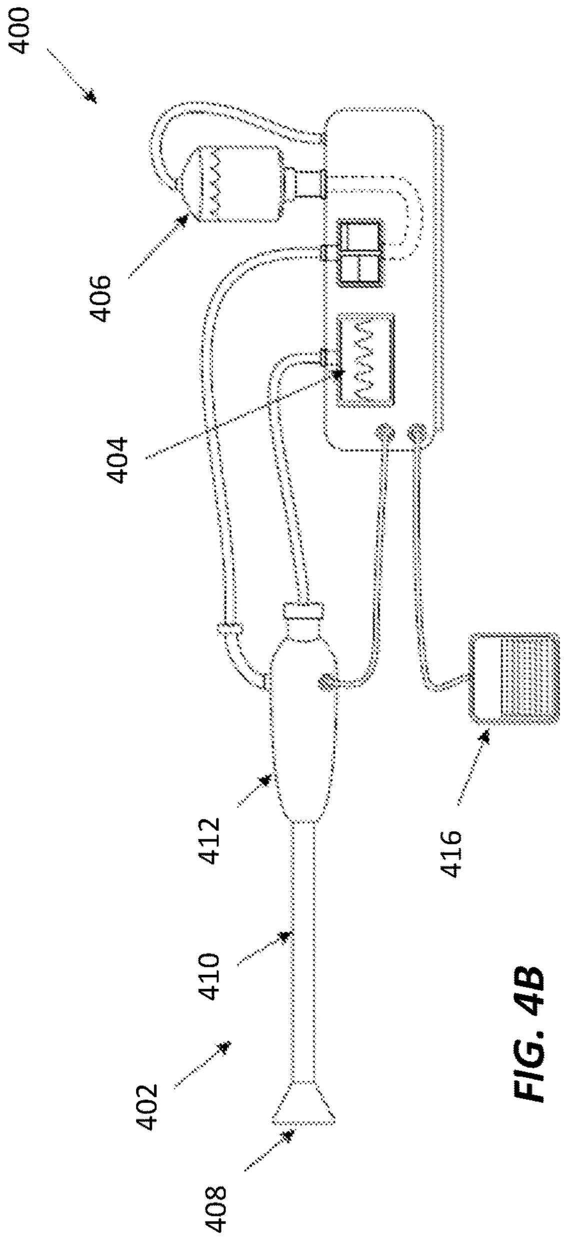
Figure 4C:
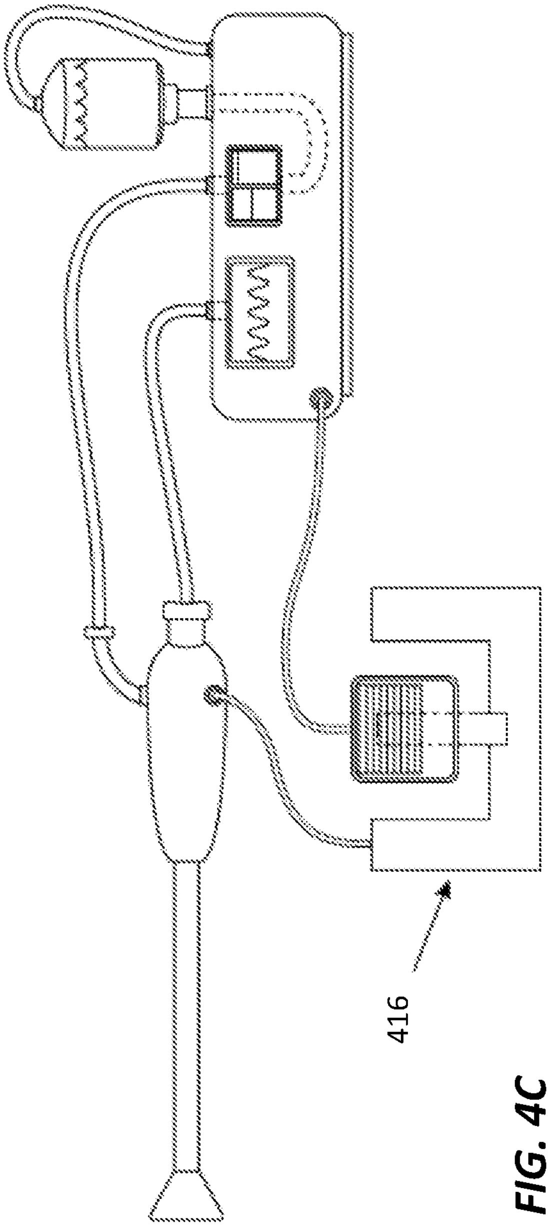

FIGS. 4A-4C illustrate various configurations of a thrombus removal system 400, including a thrombus removal device, 402, a vacuum source and cannister 404, a fluid source 406, and a pump 407. In some embodiments, the vacuum source and cannister and the fluid source are housed in a console unit that is detachably connected to the thrombus removal device. A fluid pump can be housed in the console, or alternatively, in the handle of the device. The console can include one or more CPUs, electronic controllers, or microcontrollers configured to control all functions of the system. The thrombus removal device 402 can include a funnel 408, a flexible shaft 410, a handle 412, and one or more controls 414 and 416. For example, in the embodiment shown in FIG. 4A, the device can include a finger switch or trigger 414 and a foot pedal or switch 416. These can be used to control aspiration and irrigation, respectively. Alternatively, as shown in the embodiment of FIG. 4B, the device can include only a foot switch 416, which can be used to control both functions, or in FIG. 4C, the device can include only an overpedal 416, also used to control both functions. It is also contemplated that an embodiment could include only a finger switch to control both aspiration and irrigation functions. As shown in FIG. 4A, the vacuum source and cannister 404 can be coupled to the aspiration lumen of the device with a vacuum line 418. Any clots or other debris removed from a patient during therapy can be received by, and stored in, the vacuum cannister 404 for later disposal. Similarly, the fluid source 406 (e.g., a saline bag) can be coupled to the fluid lumens of the device with a fluid line 420 for delivery of high-pressure and velocity fluid streams or jets at the base of funnel 408 to fragment thrombus material engaged by funnel 408, as described above.

Still referring to FIG. 4A, electronics line 422 can couple any electronics/sensors, etc. from the device to the console/controllers of the system. The system console including the CPUs/electronic controllers can be configured to monitor fluid and pressure levels and adjust them automatically or in real-time as needed. In some embodiments, the CPUs/electronic controllers are configured to control the vacuum and irrigation as well as electromechanically stop and start both systems in response to sensor data, such as pressure data, flow data, etc.

Prior to introduction of the thrombus removal device into a patient's blood vessel, the system is primed to remove air by pumping fluid through fluid lumen 45, manifold 25, ports 30, aspiration lumen 55, and vacuum line 418. During a thrombus removal procedure, the thrombus removal device is advanced into the patient's blood vessel, and the funnel is expanded to engage the thrombus. Pressurized fluid is delivered from fluid source 406 and pump 407 through fluid line 420 and fluid lumen 45 to manifold 25 and ports 30. In some embodiments, a media source may inject, deliver, or introduce particulate media into the fluid stream/fluid line(s). Simultaneously, vacuum is applied to aspiration lumen 55 by vacuum source and cannister 404. When a clot is engaged, the material flowing proximally through aspiration lumen 55 to the vacuum source and cannister is primarily fluid and/or media delivered through ports 30 combined with any blood that is able to pass around the engaged thrombus. As the fluid jets begin to break up the thrombus, thrombus material is pulled proximally through aspiration lumen 55 along with the injected fluid and any blood that can pass into the funnel around the thrombus. After the thrombus has been broken up sufficiently to become dislodged from the blood vessel, the remaining thrombus material moves proximally toward the vacuum source and cannister 604.

In some embodiments, the controller can reduce the strength of the vacuum applied to the aspiration lumen after a thrombus has been detected in the vacuum line so that blood loss is minimized.

As is described above, aspiration occurs down the central lumen of the device and is provided by a vacuum pump in the console. The vacuum pump can include a container that collects any thrombus or debris removed from the patient.

Approaches described herein can comprise particles provided via a fluid carrier (e.g., particulate media) that are directed with high force toward a thrombus, enhancing the effects of irrigation and facilitating thrombus fragmentation and/or erosion. The particulate media may be provided within a separate channel or lumen. The particulate media may be combined with the pressurized fluid in the fluid lumen.

Figure 5A:
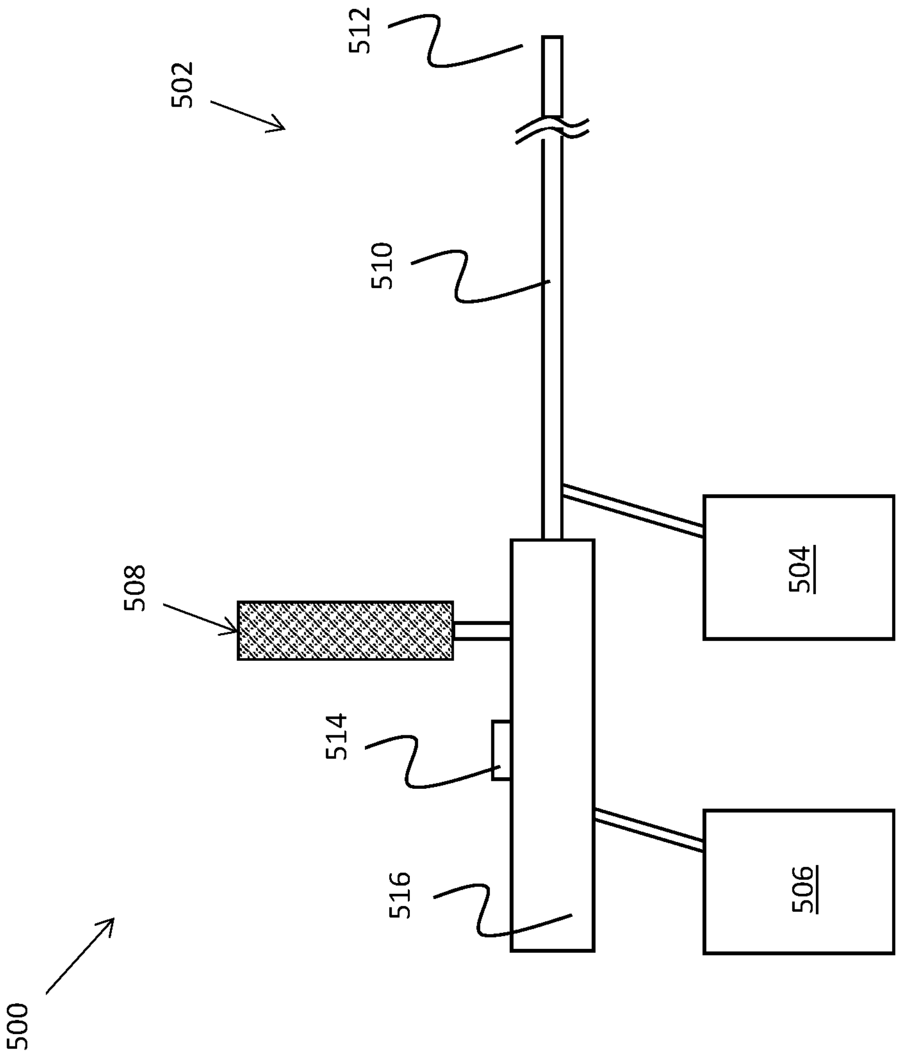

FIG. 5A illustrates a configuration of a thrombus removal system 500 that includes a thrombus removal device 502, a vacuum source and cannister 504, an irrigation source 506, and a particulate media source 508. In some embodiments, the vacuum source and cannister, the fluid source, and/or the particulate media source are housed in a console unit that is detachably connected to the thrombus removal device. The thrombus removal device can further include a flexible catheter shaft 510 terminating at a distal portion 512. As described above, the distal end can include a funnel (not shown). An aspiration lumen can extend from the distal end of the catheter shaft to the vacuum source and cannister 504. Separate fluid lumen(s) (not illustrated, but described above) can extend within the shaft to the fluid source 506. The fluid lumen(s) can terminate at fluid or jet ports near the distal end of the device (or in the funnel of the device) to produce one or more fluid or jet streams. The thrombus removal device can include one or more controls 514, such as buttons, levers, knobs, dials, triggers, or the like. These controls can be used to separately control aspiration, irrigation, and introduction of particulate media. In some embodiments the controls are on a handle 516 of the thrombectomy device. In other embodiments, the controls are on a console, or optionally, a remote coupled to the device and/or console.

FIG. 5B shows one embodiment of a media source 508. The media source can include one or more valves 518, a regulator 520, a mixing chamber 522, a fluid inlet 524, media inlet 526, and a media output 528. The fluid inlet can be coupled to the irrigation fluid source previously described, or a separate fluid inlet. The media inlet can be coupled to a source of media (not shown). In some embodiments, the media output is configured to actively introduce particulate media into the fluid stream of the thrombus removal device (e.g., via a pump). In some embodiments, the particulate media is passively introduced into the device, via gravity or a pressure gradient (e.g., Venturi effect). In some embodiments, the one or more valves can be operatively controlled (either manually, or automatically by the system) to selectively introduce fluid and/or particulate media into the mixing chamber. For example, if a non-particulate media fluid stream is desired, the one or more valves can be controlled to introduce only fluid (e.g., saline) into the mixing chamber and prevent particulate media from entering the mixing chamber, and therefore the thrombectomy device. On the other hand, both fluid and particulate media can be introduced into the mixing chamber, via the one or more valves, to fluidize the particulate media for delivery with the thrombectomy device. FIGS. 5C-5D illustrate additional embodiments of a mixing chamber with a number of ports that can be used for the fluid inlet, media inlet, and media output.

Figure 6A:
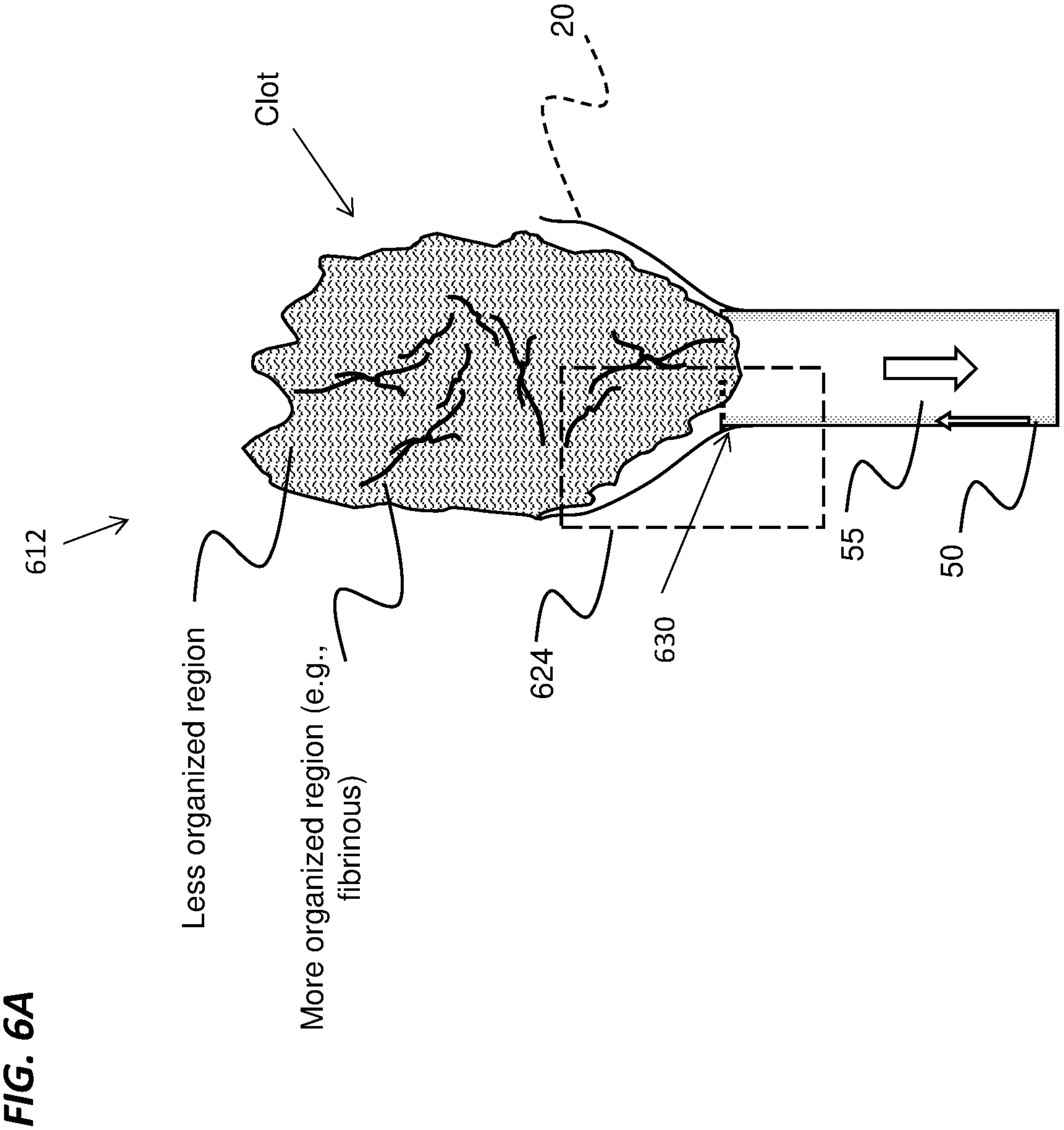
FIGS. 6A-6D illustrate an embodiment of a thrombus removal system including a fluid source, an aspiration system, a particulate media source, and one or more controls for controlling irrigation and/or aspiration of the system.

FIGS. 6A-6D illustrate a distal portion 612 of a thrombus removal system according to an embodiment of the present disclosure. FIG. 6A illustrates an elevation sectional view of the distal portion. The example in FIG. 6A depicts a (e.g., optional) expandable and collapsible funnel 20 that is positioned at the distal end of the device, the distal end adapted to engage with thrombus and/or a tissue (e.g., vessel) wall to aid in thrombus fragmentation and/or removal. The thrombus removal device includes an aspiration lumen 55 that is generally centrally located. A generally annular volume forms at least one fluid lumen 50 between an outer wall and an inner wall of the thrombus removal device. The fluid lumen is adapted for fluid communication with a fluid delivery mechanism. One or more irrigation apertures 630 (e.g., nozzles, orifices, or ports) are positioned in the thrombus removal system to be in fluid communication with the fluid lumen. In operation, the apertures are adapted to direct (e.g., pressurized) fluid toward thrombus that is engaged with the distal portion of the thrombus removal system.

As shown in FIG. 6A, an organized clot is disposed within the funnel of the thrombus removal device. The organized clot includes regions of relatively greater cohesion (e.g., more organized), and regions of relatively lesser cohesion (e.g., less organized). In some cases, an organized clot is resistant to fragmentation and removal even when subjected to aspiration and/or irrigation.

Figure 6B:
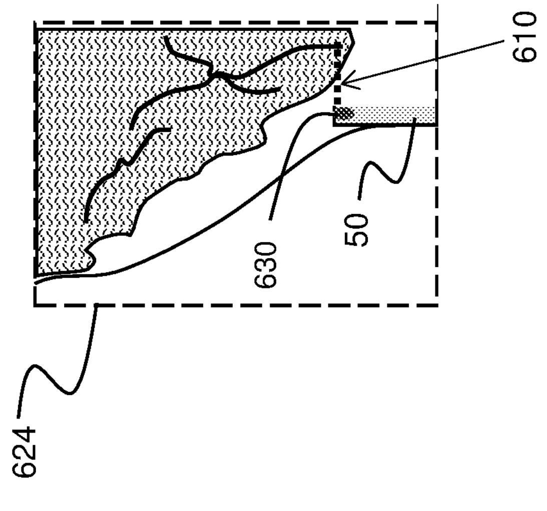
Figure 6C:
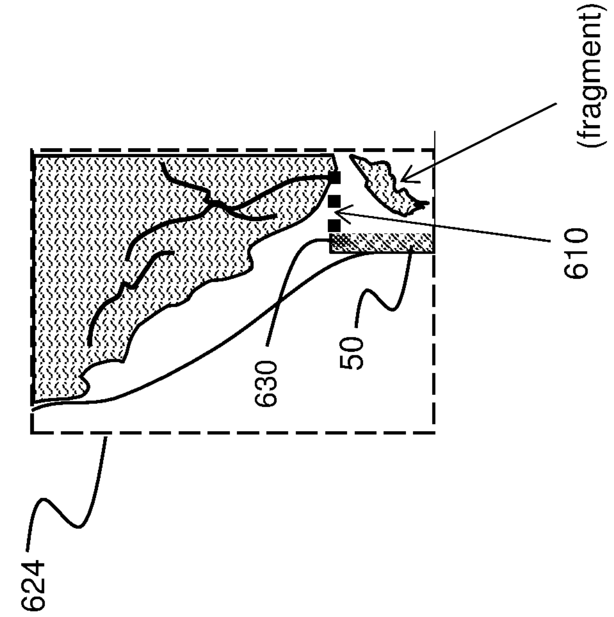
Figure 6D:
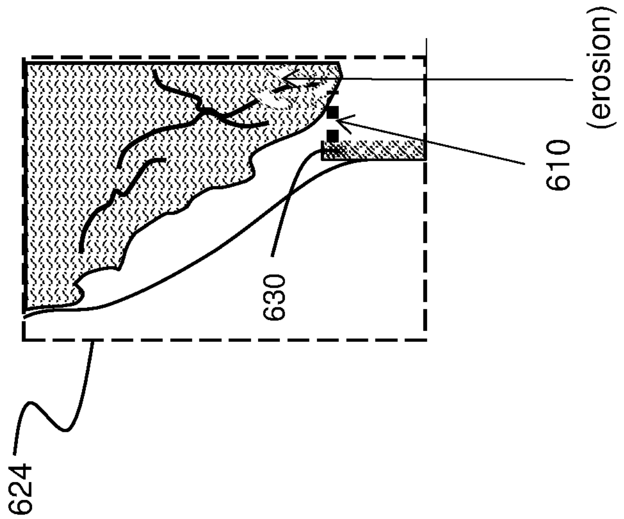

FIGS. 6B-6D depict a close-up view of region 624 from FIG. 6A. In FIG. 6B, an example of a thrombus removal device is shown wherein a pressurized fluid stream 610 impinges upon the organized clot, without fragmentation or clearance thereof. In this example, the fluid stream 610 and fluid lumen 50 include only a pressurized fluid, such as saline.

As depicted in FIGS. 6C and 6D, particulate material can advantageously be used to facilitate fragmentation and/or erosion of the thrombus, and lead to its clearance. The particulate material can be provided as particulate media, that is, in a fluidized form. In some embodiments, one or more materials (e.g., particles, or gases) are mixed with the irrigation fluid (e.g., saline) to provide the particulate media. This mixed stream of particulate media and irrigation fluid can be delivered, for example, through the fluid lumen and ports/apertures previously described herein and used for fluid/saline jetting. In some embodiments, the particulate media is directed along a separate particulate media lumen (e.g., the auxiliary lumens described above) and through a particulate media aperture distinct from the fluid stream lumens and apertures to impinge upon the thrombus. In some embodiments, the particulate media is provided (e.g., selectively) into the irrigation lumen and through irrigation apertures. The addition of particulate media to the pressurized fluid streams can induce (e.g., increased) shear forces acting upon the thrombus. The particulate media can provide impact forces that dislodge less organized portions of the thrombus from more organized regions, reducing its cohesion and thereby eroding the thrombus. When the particulate media comprise a solubilized gas, bubbles are generated from the solubilized gas when it comes out of solution as the particulate media (e.g., carrier) transitions from a (e.g., initial) carrier temperature and pressure to a blood temperature and pressure. In consideration of tissue trauma prevention, fluid streams having particulate media are generally directed within a volume defined by the thrombus removal system—for example, within a distal end and/or a funnel. In some embodiments, the speed and/or momentum of the particles carries them across the catheter to impinge upon an opposing inner wall in an impact zone. In some embodiments, the catheter comprises regions of reinforced construction (e.g., embedded alloys or fibers) in the impact zone.

In general, particles as described herein are selected such that they can be introduced via the thrombus removal device as an abrasive mixture (to fragment thrombus), yet can then readily be removed from the body. Readily removed can include being aspirated by the thrombus removal device, and/or dissolved within the body. Examples of materials that may be used to formulate the particular media are salts (e.g., sodium chloride, calcium chloride), sugar, contrast media, sodium lactate solution, carbonation/carbon dioxide (e.g., supercritical carbon dioxide), helium, argon, and embolic- or glass-microparticles ("beads" or "microbeads"). The particles may include a coating (e.g., a lipid coating) that affects dissolution of the particles within the carrier fluid and/or the body. For example, the coating may reduce a rate of dissolution of the particles within the carrier fluid, while promoting dissolution of the particles in the body. The coating can provide a pH that varies from the pH of the blood by at least about 5%, at least about 10%, or at least about 20%. The particles can be heparinized. In some embodiments, salt particles can be provided in a briny solution to reduce dissolution during delivery. The briny solution can comprise a salinity from at least 1.5% to at least about 3%.

As mentioned above, in some embodiments, the jets/fluid streams can comprise fluid without particulate media (e.g., saline), or fluidized particulate media. The various fluid streams can be delivered through the same apertures/lumens, or the device can include dedicated lumens and apertures for particulate media and dedicated lumens and apertures for non-particulate fluid (e.g., saline) jetting and delivery. During a thrombectomy procedure, it may be desirable to first try to remove a clot with only standard fluid jetting (e.g., saline). If a user or the system determines that clot is not being removed, then the system can switch to injecting or delivering particulate media to attempt to break up or remove the clot.

In various embodiments, the system can have an average flow velocity within the fluid lumen of at least 20 m/s to achieve consistent and successful aspiration of clots. In some embodiments, the fluid source itself can be delivered in a pulsed sequence or a preprogrammed sequence that includes some combination of pulsatile flow and constant flow to deliver fluid to the jets. In these embodiments, while the average pulsed fluid velocity may be at least 20 m/s, the peak fluid velocity may be up to double the average pulsed velocity (e.g., 40 m/s or more) during the pulsing of the fluid source. In some embodiments, the fluid and/or particulate media apertures are about 0.0200", 0.0100", 0.008" or 0.006". In some embodiments, particles have an average diameter that is at least about 5%, at least about 10%, or at least about 50% smaller than the diameter of the particulate media aperture(s). In some embodiments particulate media is provided at about 5 meters/sec, about 15 meters/sec, or about 30 meters/sec from apertures toward the thrombus. The particulate media can be provided at any speed within the aforementioned range of speeds.

The thrombus removal system can be sized and configured to access and remove thrombi in various locations or vessels within a patient's body. It should be understood that while the dimensions of the system may vary depending on the target location, generally the same features and components described herein will be implemented in the thrombus removal system regardless of the application. For example, a thrombus removal system configured to remove pulmonary embolism (PE) from a patient may have an outer wall/tube with a size of approximately 11-13 Fr, or preferably 12 Fr, and an inner wall/tube with a size of 7-9 Fr, or preferably 8 Fr. A deep vein thrombosis (DVT) device, on the other hand, may have an outer wall/tube with a size of approximately 9-11 Fr, or preferably 10 Fr, and an inner wall/tube with a size of 6-9 Fr, or preferably 7.5 Fr. Applications are further provided for ischemic stroke and peripheral embolism applications.

Figure 7:
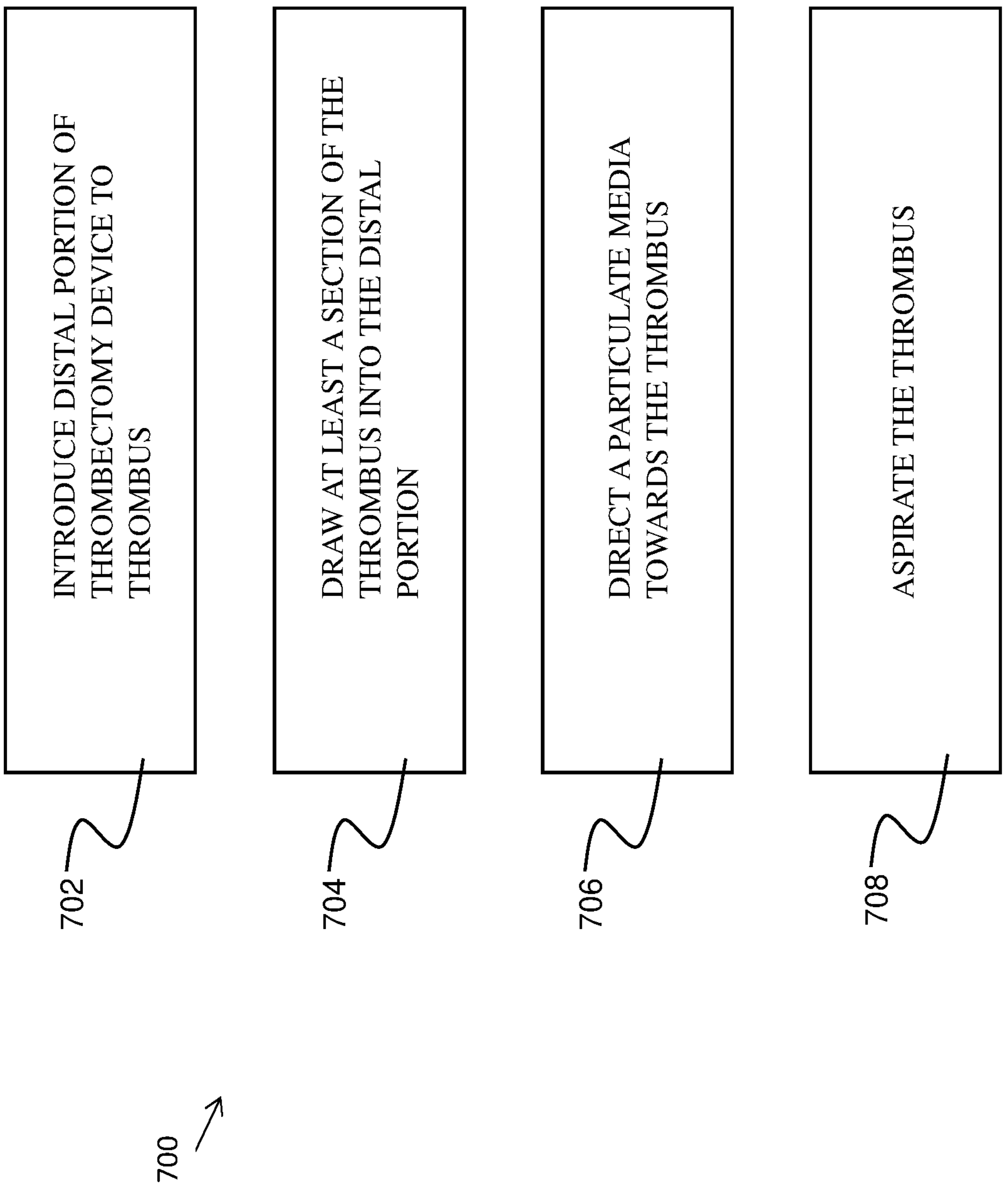
FIG. 7 is a flowchart describing a thrombectomy method.

FIG. 7 is a flowchart illustrating a method 700 that includes a thrombectomy method for breaking up, macerating, cutting, and/or removing a thrombus from a blood vessel of a subject. At step 702, the method can include introducing a distal portion of an elongate catheter to a thrombus in a blood vessel, such as a pulmonary artery. In some examples, introducing the distal portion is into the blood vessel in a low-profile configuration, and wherein the method further comprises expanding the distal portion into a deployed configuration. In some embodiments, the distal portion can comprise an expandable funnel.

At step 704, the method can further include drawing at least a section of the thrombus into the distal portion. In some examples, drawing at least a section of the thrombus into the distal portion can comprise drawing the thrombus into an expandable funnel. In some examples, drawing the thrombus into the distal portion comprises applying vacuum to the distal portion to aspirate the thrombus into the distal portion.

At step 706, the method can include directing a particulate media towards the thrombus. In some examples, directing the particulate media towards the thrombus further comprises combining the particulate media with a pressurized fluid. In other embodiments, directing the particulate media further comprises delivering a fluid to a mixing chamber, delivering the particulate media to the mixing chamber, and fluidizing the particulate media in the mixing chamber with the fluid. In some examples, directing the particulate media into the thrombus further comprises directing the particulate media along at least two intersecting paths.

At step 708, the method can include aspirating the thrombus out of the blood vessel. In some examples, aspirating the thrombus out of the blood vessel comprises applying vacuum to the distal portion to aspirate the thrombus out of the blood vessel. In some embodiments, aspirating the thrombus comprises aspirating chunks, fragments, or pieces of the thrombus.

The method can further comprise directing a fluid stream towards the thrombus. For example, the fluid stream may be directed towards the thrombus with one or more fluid stream apertures and the particulate media may be directed towards the thrombus with one or more particulate media apertures. In some embodiments, the fluid stream is carried within one or more fluid lumens in the elongate catheter and the particulate media is carried within one or more particulate media lumens in the elongate catheter.

The particulate media can be various types of media. In some embodiments, the particulate media is an abrasive mixture, comprises salt, comprises sugar, is a contrast media, comprises lactated ringers, comprises microparticles, comprises microbeads, or includes a coating configured to reduce dissolution of the particulate media within the body. The coating can be a lipid coating, for example.

While the embodiments herein have been described as being intended to remove thrombi from a patient's vasculature, other applications of this technology are provided. For example, the devices described herein can be used for breaking up and removing hardened stool from the digestive tract of a patient, such as from the intestines or colon of a patient. In one embodiment, the device can be inserted into a colon or intestine of the patient (such as through the anus) and advanced to the site of hardened stool. Next, the aspiration system can be activated to engage the hardened stool with an engagement member (e.g., funnel) of the device. Finally, the jets or irrigation can be activated to break off pieces of the hardened stool and aspirate them into the system. Any of the techniques described above with respect to controlling the system or removing clots can be applied to the removal of hardened stool.

As one of skill in the art will appreciate from the disclosure herein, various components of the thrombus removal systems described above can be omitted without deviating from the scope of the present technology. As discussed previously, for example, the present technology can be used and/or modified to remove other types of emboli that may occlude a blood vessel, such as fat, tissue, or a foreign substance. Further, although some embodiments herein are described in the context of thrombus removal from a pulmonary artery, the disclosed technology may be applied to removal of thrombi and/or emboli from other portions of the vasculature (e.g., in neurovascular, coronary, or peripheral applications). Likewise, additional components not explicitly described above may be added to the thrombus removal systems without deviating from the scope of the present technology. Accordingly, the systems described herein are not limited to those configurations expressly identified, but rather encompasses variations and alterations of the described systems.

Conclusion

The above detailed description of embodiments of the technology are not intended to be exhaustive or to limit the technology to the precise forms disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Unless the context clearly requires otherwise, throughout the description and the examples, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. As used herein, the phrase "and/or" as in "A and/or B" refers to A alone, B alone, and A and B. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

What is claimed is:

1. A thrombectomy method, comprising:

delivering a distal portion of an elongate catheter into proximity with a thrombus in a blood vessel;

engaging the distal portion with the thrombus; and directing a particulate media towards the thrombus along at least two intersecting paths.

2. The method of claim 1, further comprising aspirating the thrombus out of the blood vessel.

3. The method of claim 1, wherein directing the particulate media towards the thrombus further comprises combining the particulate media with a pressurized fluid.

4. The method of claim 1, further comprising directing a fluid stream towards the thrombus.

5. The method of claim 4, wherein the fluid stream is directed towards the thrombus with one or more fluid stream apertures and the particulate media is directed towards the thrombus with one or more particulate media apertures.

6. The method of claim 4, wherein the fluid stream is carried within one or more fluid lumens in the elongate catheter and the particulate media is carried within one or more particulate media lumens in the elongate catheter.

7. The method of claim 1, wherein the particulate media is an abrasive mixture.

8. The method of claim 1, wherein the particulate media comprises a salt.

9. The method of claim 1, wherein the particulate media comprises a sugar.

10. The method of claim 1, wherein the particulate media comprises a contrast media.

11. The method of claim 1, wherein the particulate media comprises lactated ringers.

12. The method of claim 1, wherein the particulate media comprises microparticles.

13. The method of claim 1, wherein the particulate media comprises microbeads.

14. The method of claim 1, wherein the particulate media includes a coating configured to reduce dissolution of the particulate media within the body.

15. The method of claim 14, wherein the coating is a lipid coating.

16. The method of claim 1, wherein directing the particulate media further comprises:

delivering a fluid to a mixing chamber;

delivering the particulate media to the mixing chamber; and fluidizing the particulate media in the mixing chamber with the fluid.

17. The method of claim 1, wherein delivering the distal portion further comprises delivering the distal portion into the blood vessel in a low-profile configuration, and wherein the method further comprises expanding the distal portion into a deployed configuration.

18. The method of claim 1, wherein the blood vessel comprises a pulmonary artery.

19. A thrombectomy method, comprising:

delivering a distal portion of an elongate catheter into proximity with a thrombus in a blood vessel;

engaging the distal portion with the thrombus;

delivering a fluid to a mixing chamber;

delivering a particulate media to the mixing chamber;

fluidizing the particulate media in the mixing chamber with the fluid; and directing the fluidized particulate media towards the thrombus.

* * * * *